US007223411B1

(12) United States Patent
Knipe et al.

(10) Patent No.: US 7,223,411 B1
(45) Date of Patent: May 29, 2007

(54) HERPESVIRUS REPLICATION DEFECTIVE MUTANTS

(75) Inventors: David Knipe, Auburndale, MA (US); Robert Finberg, Canton, MA (US); George Siber, Brookline, MA (US)

(73) Assignees: Dana-Farber Cancer Institute, Boston, MA (US); President & Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/278,601

(22) Filed: Jul. 21, 1994

Related U.S. Application Data

(63) Continuation-in-part of application No. 08/179,106, filed on Jan. 10, 1994, now abandoned, which is a continuation-in-part of application No. 07/922,912, filed on Jul. 31, 1992, now abandoned.

(51) Int. Cl.
*A61K 39/245* (2006.01)
(52) U.S. Cl. .............................. 424/229.1; 424/199.1; 435/320.1
(58) Field of Classification Search ............. 424/205.1, 424/229.1, 230.1, 231.1, 232.1, 233.1, 199.1, 424/93.2; 435/235.1, 236, 320.1
See application file for complete search history.

(56) References Cited

U.S. PATENT DOCUMENTS

| 4,554,159 | A |   | 11/1985 | Roizman et al. ............... 424/89 |
| 4,769,331 | A |   | 9/1988 | Roizman et al. .......... 435/172.3 |
| 4,859,587 | A |   | 8/1989 | Roizman ...................... 435/68 |
| 5,288,641 | A |   | 2/1994 | Roizman ................. 435/320.1 |
| 5,328,688 | A |   | 7/1994 | Roizman ................. 424/205.1 |
| 5,658,724 | A | * | 8/1997 | DeLuca .......................... 435/5 |
| 5,665,362 | A |   | 9/1997 | Inglis et al. |
| 5,804,413 | A | * | 9/1998 | DeLuca ...................... 435/69.1 |
| 5,837,261 | A | * | 11/1998 | Inglis et al. ............. 424/229.1 |
| 5,879,934 | A | * | 3/1999 | DeLuca ................... 435/320.1 |
| 6,541,009 | B1 | * | 4/2003 | Inglis et al. ............. 424/199.1 |

FOREIGN PATENT DOCUMENTS

| EP | 0213894 | 8/1986 |
| EP | 0277773 | 1/1988 |
| EP | 0386882 | 2/1990 |
| EP | 0453242 | 4/1991 |
| WO | 89/09271 | 10/1989 |
| WO | 90/05538 | 5/1990 |
| WO | 91/05055 | 4/1991 |
| WO | 92/05263 | 4/1992 |
| WO | WO94/01573 | 1/1994 |
| WO | WO94/03207 | 2/1994 |
| WO | WO94/03595 | 2/1994 |
| WO | WO94/21807 | 9/1994 |

OTHER PUBLICATIONS

McCarthy et al. J. Virol. 63(1): 18-27 Jan. 1989.*
Bostock (Vet. Microbiol. 23:55-71, Jun. 1990). Abstract only cited.*
Bostock (Vet. Microbiol. 23:55-71, Jun. 1990).*
Dobson et al (Neuron 5:353-60, 1990).*
Cartwright (TIBTECH 5:25-30, 1987).*
Katz et al (Journal of Virology 64:4288-4295, 1990).*
Shih, Meng-Fu et al., "Expression of hepatitis B virus S gene by herpes simplex virus type 1 vectors carrying α- and β-regulated gene chimeras," *Proc. Natl. Acad. Sci. USA*, 81:5867-5870, (1984).
Coutelier, Jean-Paul et al., "IgG2a restriction of murine antibodies elicited by viral infections," *J. Exp. Med.*, 165:64-69 (1987).
Coutelier, Jean-Paul et al., Brief Definitive Report, "Virally induced modulation of murine IgG antibody subclasses," *J. Exp. Med.*, 166:2373-2378 (1988).
Nguyen, Lien H. et al., "Replication-Defective Mutants of Herpes Simplex Virus (HSV) Induce Cellular Immunity and Protect against Lethal HSV Infection," *J. Virol.*, 66(12) :7067-7072 (1992).
Kipps, Thomas J. et al., "Importance of immunoglobulin isotype in human antibody-dependent, cell-mediated cytotoxicity directed by murine monoclonal antibodies," *J. Exp. Med.*, 161:1-17 (1985).
Gao, Min and Knipe,, David M., "Genetic Evidence for Multiple Nuclear Functions of the Herpes Simplex Virus ICP8 DNA-Binding Protein," *Journal of Virology*, 63(12):5258-5267, (1989).
Cunningham, Charles et al., "The UL13 virion protein of herpes simplex virus type 1 is phosphorylated by a novel virus-induced protein kinase," *Journal of General Virology*, 73:303-311, (1992).
Stevenson, David et al., "Characterization of the varicella-zoster virus gene 61 protein," *Journal of General Virology*, 73:521-530, (1992).
Ali, Mir A. et al., "Enhanced malignant transformation induced by expression of a distinct protein domain of ribonucleotide reductase large subunite from herpes simplex virus type 2," *Proc. Natl. Acad. Sci. USA*, 88:8257-8261, (1991).
Rice, Stephen A. and Knipe, David M., "Genetic Evidence for Two Distinct Transactivation Functions of the Herpes Simplex Virus α Protein ICP27," *J. Virol.*, 64:1704-1715, (1990).
Rice, Stephen A. et al., "Herpes Simplex Virus Alpha Protein ICP27 Possesses Separable Positive and Negative Regulatory Activities," *J. Virol.*, 63:3399-3407, (1989).
"Fowlpox Virus: A 'Live-Dead' Vaccine Vector," *ASM News*, 58 (5):257, (1992).

(Continued)

*Primary Examiner*—Ali R. Salimi
(74) *Attorney, Agent, or Firm*—George W. Neuner; Edwards Angell Palmer & Dodge LLP

(57) ABSTRACT

A herpesvirus vaccine comprising a mutated herpesvirus suspended in a pharmaceutically acceptable carrier. The mutated herpesvirus is capable of infecting cells of the mammal to be vaccinated, but incapable of completing a replicative cycle, and it is capable of eliciting a protective immune response in that mammal. The mutated herpesvirus is also capable of treating immunomodulatory or immuno-regulatory diseases. The mutation occurs in at least one gene encoding a protein essential for replication of the virus, so that the mutation renders the virus replication defective.

38 Claims, 12 Drawing Sheets

OTHER PUBLICATIONS

Quinn, John P. and McGeoch, Duncan J., "DNA sequence of the region in the genome of herpes simplex virus type 1 containing the genes for DNA polymerase and the major DNA binding protein," *Nucleic Acids Research*, 13(22):8143-8163, (1985).

Sacks, Wendy R. et al., "Herpes Simplex Virus Type 1 ICP27 Is an Essential Regulatory Protein," *J. Virol.*, 55(3):796-805, (1985).

Baer, R. et al., "DNA sequence and expression of the B95-8 Epstein-Barr virus genome," *Nature*, 310:207-211, (1984).

Galloway, Denise A. et al., "Small fragments of herpesvirus DNA with Transforming activity contain insertion sequence-like structures," *Proc. Natl. Acad. Sci. USA*, 81:4736-4740, (1984).

Weller, Sandra K. et al., "Genetic Analysis of Temperature-Sensitive Mutants Which Define the Gene for the Major Herpes Simplex Virus Type 1 DNA-Binding Protein," *J. Virol.*, 45(1):354-366, (1983).

Farrell, H. et al., "Vaccine potential of a herpes simplex virus mutant lacking an essential glycoprotein," Abstract, *17th International Herpesvirus Workshop*, Edinburgh, Scotland, p. 378, (Aug. 1-7, 1992).

McLean, L. et al., "Protective vaccination with a gH-deleted HSV-1 virus," *18th International Herpesvirus Workshop*, Pittsburgh, PA, p. C-71, (Jul. 25-30, 1993).

DeLuca, Neal A. et al., "Isolation and Characterization of Deletion Mutants of Herpes Simplex Virus Type 1 in the Gene Encoding Immediate-Early Regulatory Protein ICP4," *J. Virol.*, 56(2):558-570, (1985).

Emi, Nobuhiko et al., "Pseudotype Formation of Murine Leukemia Virus with the G Protein of Vesicular Stomatitis Virus," *J. Virol.*, 65(3): 1202-1207, (1991).

Jayaraman, Sundararajan et al., "Exacerbation of Murine Herpes Simplex Virus-Mediated Stromal Keratitis by Th2 Type T Cells," *Journal of Immunology*, 151(10):5777-5789, (1993).

Marchetti, Michael E. et al., "A Temperature-Sensitive Mutation in a Herpes Simplex Virus Type 1 Gene Required for Viral DNA Synthesis Maps to Coordinates 0.609 through 0.614 in $U_L$," *J. Virol.*, 62(3):715-721, (1988).

Ligas, Michael W. and Johnson, David C., "A Herpes Simplex Virus Mutant in Which Glycoprotein D Sequences Are Replaced by β-Galactosidase Sequences Binds to but Is Unable to Penetrate into Cells," *J. Virol.*, 62(5):1486-1494, (1988).

Farrell, H. E. et al., "Vaccine Potential of a Herpes Simplex Virus Type 1 Mutant with an Essential Glycoprotein Deleted," *J. Virology*, 68(2):927-932, (1994).

Morrison, Lynda A. and Knipe, David M., "Immunization with Replication-Defective Mutants of Herpes Simplex Virus Type 1: Sites of Immune Intervention in Pathogenesis of Challenge Virus Infection," *J. Virol.* 68:689-696 (1994).

Nguyen, Lien et al., "Mechanism of Virus-Induced Ig subclass Shifts," *J. Immunol.* 152:478-484 (1994).

Robertson, L.M., et al., "Peripheral replication and latency reactivation kinetics of the non-neurovirulent herpes simplex virus type 1 variant 1716," *Journal of General Virology*, 73:967-970(1992).

* cited by examiner

US 7,223,411 B1

HERPESVIRUS REPLICATION DEFECTIVE MUTANTS

RELATED APPLICATIONS

This application is a Continuation-in-Part of U.S. application Ser. No. 08/179,106, filed Jan. 10, 1994 now abandoned, which is a Continuation-in-Part of U.S. application Ser. No. 07/922,912, filed Jul. 31, 1992 now abandoned, both of which are incorporated herein by reference.

GOVERNMENT SUPPORT

This invention was made with the support from the U.S. Government which has certain rights to the invention.

BACKGROUND OF THE INVENTION

Herpesviruses are enveloped double stranded DNA-containing viruses in an icosahedral nucleocapsid. At least seven herpesviruses are associated with infection in humans, including herpes simplex virus type-1 (HSV-1), herpes simplex virus type-2 (HSV-2), varicella zoster virus (VZV), Epstein Barr virus (EBV), cytomegalovirus (CMV), human herpesvirus-6 (HHV-6) and human herpesvirus-7 (HHV-7).

HSV-1 is one of the most intensively studied herpesviruses. HSV-1 exhibits a pattern of gene expression during productive infection which is stringently regulated (Fields et al. *Virology*, 1990, Raven Press, NY). The more than 70 genes identified in this virus are classified in part according to the kinetics of their expression. Expression of each class of genes is dependent upon expression of genes from the preceding class. The viral immediate early, or $\alpha$, genes are expressed first, followed by the viral early, or $\beta$, genes which in turn are followed by the late, or $\gamma$, genes. The $\gamma$ genes are further subdivided into $\gamma$-1 and $\gamma$-2 genes, depending upon the extent to which their expression relies upon viral DNA replication.

Several viral proteins have been shown to regulate expression of HSV-1 genes. The ICP4 protein is essential for $\beta$ and $\gamma$ gene expression (DeLuca et al., *J. Virol.*, 56:558 (1985)). The ICP27 protein is required for $\gamma$ gene expression and for viral DNA replication (McCarthy et al., *J. Virol.*, 63:18 (1989)). The major DNA-binding protein (ICP8), a $\beta$ gene product, is also required for viral DNA replication and for $\gamma$ gene expression (Gao et al., *J. Virol.* 63:5258 (1989); Quinlan et al., *Cell*, 36:657 (1984)).

Diseases caused by herpesviruses in humans vary from mild to severe, and in some cases, infection with these viruses is life-threatening.

Vaccination is a common approach to prevention of disease. Various vaccines based on isolated immunogens, and on live, attenuated virus have been proposed for herpesviruses (Roizman, U.S. Pat. No. 4,859,587; and Meignier et al., *J. Inf. Dis.*, 3:603-613 (1988) (HSV); Takahasi et al., *Biken J.*, 18:25-33 (1975) (VZV); Elek et al., *Lancet*, 1:1-5 (1974); and Plotkin et al. *Infect. Immun*, 12:521-527 (1975) (CMV)).

Further, development of therapeutic immunomodulants for treating immunopathologic diseases, such as herpetic stromal keratitis, would be desirable (Jayaraman et al., *J. of Immunology*, 151:5777-5789, Nov. 15, 1993).

SUMMARY OF THE INVENTION

The invention features a herpesvirus vaccine comprising a mutated herpesvirus in a pharmaceutically acceptable carrier. The mutated herpesvirus is capable of infecting cells of the mammal to be vaccinated, and it is capable of eliciting a protective immune response in that mammal and/or inducing an immunomodulatory response as evidenced by an antibody subclass shift when administered in vivo to that mammal. The mutation occurs in at least one gene encoding a protein essential for replication of the virus, so that the mutation renders the virus replication defective. The mutated virus is live in the sense that it retains the ability to infect target cells in the host to be protected. Infection will not produce progeny, yet the virus elicits a protective immune response, e.g., via virally induced or encoded immunogens produced by infected cells. Protection means that the host mounts an immune response to the vaccine so that subsequent infection by wild-type virus is prevented or is less severe in terms of duration and extent. Preferably, establishment of latent infection is prevented.

In preferred embodiments, the herpesvirus is HSV-1, HSV-2, VZV, EBV, CMV, HHV-6, HHV-7 or the non-human equine herpesvirus type-1. Preferably, the mutation is in the gene encoding HSV-1 ICP27 or HSV-1 ICP8, or the corresponding genes in a non-HSV-1 herpesvirus. A preferred mutant herpesvirus for use in the vaccine is n504R or d301. More preferably, the herpesvirus contains a mutation in both the HSV-1 ICP27, and ICP8 genes or in both the corresponding genes of a non-HSV-1 herpesvirus. The mutant herpesvirus may also be engineered to include one or more heterologous genes so as to be a vaccine expression vector which induces protection against a pathogen heterologous to the parent herpesvirus. Preferably, the mutant herpesvirus includes the viral wild-type thymidine kinase gene.

The invention features methods of making a herpesvirus vaccine by constructing the above-described mutated herpesvirus and suspending it in a pharmaceutically acceptable carrier.

The invention includes immunizing a mammal against a herpesvirus by administering the above-described mutated herpesvirus vaccine. The vaccine of the claimed invention could also be used in a method of immunizing a mammal against other pathogens by administering a mutated herpes virus comprising a heterologous gene encoding an immunogen capable of eliciting a protective immune response.

The invention includes a method of treating an immunopathologic, immunomodulatory or immunoregulatory disease or condition, such as herpetic stromal keratitis, by administering to a mammal in need thereof an effective amount of the mutated herpesvirus, to induce an immunomodulatory response as evidenced by an antibody subclass shift in the mammal.

The invention includes a pharmaceutical composition for the prophylaxis or treatment of an immunopathologic disease or condition, such as herpetic stromal keratitis.

DETAILED DESCRIPTION OF THE INVENTION

Figure 1:
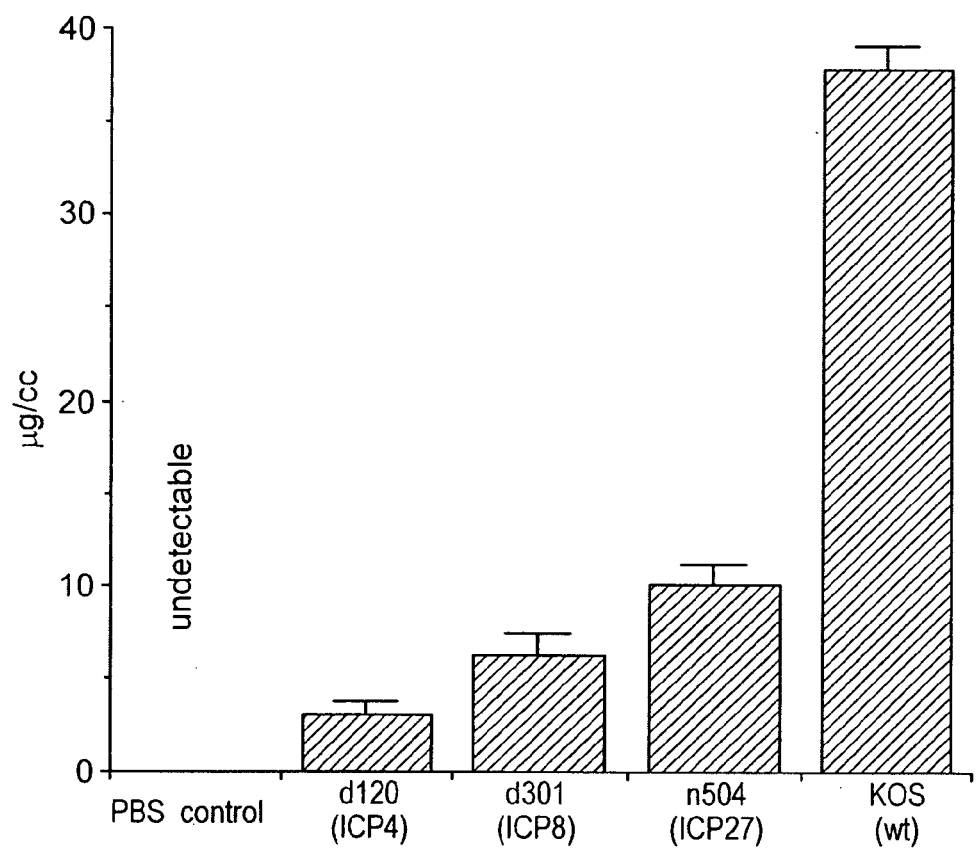
FIG. 1 is a graphical representation of the antibody response in mice inoculated with wild-type HSV-1 and with the replication defective mutants d301, n504 and d120.

The claimed invention is based on the discovery that the replication defective herpesviruses described herein result in the production of increased levels of IgG2a with a consequent IgG subclass shift, preferably, similar to that induced by live virus, upon administration. By a "subclass shift", it is meant that the ratio of IgG2a/IgG1 (by weight) increases in comparison with that observed by the administration of inactivated virus, such as UV- or psoralen-inactivated viruses, under the same conditions. Preferably, the subclass shift observed is similar to that observed by the corresponding wild-type virus, under the same conditions.

The invention is also based on the discovery that the described replication defective herpesvirus mutants elicit a protective immune response in vivo that is characterized, for example, by decreased risk of latent infection, decreased local replication and a decreased risk of central nervous system (CNS) disease.

In accordance with the invention, herpesvirus mutants useful as vaccines or therapeutics can be constructed and tested using methods, such as those described below, generally known in the art. Construction of such mutants is facilitated by the fact that the complete DNA sequences of four herpesviruses, HSV-1, VZV, EBV and CMV, are known (McGeoch et al., J. Gen. Virol., 69:1531 (1988); McGeoch et al., J. Mol. Biol., 181:1 (1985); McGeoch et al., Nucl. Acids Res. 14:1727 (1986); Davison et al., J. Gen. Virol. 67:1759 (1986); Baer et al., Nature, 310:207 (1984); Chee et al., Current Topics in Microbiol. and Immunol., 154:125 (1990)), and restriction enzyme maps, partial sequence and location of many of the genes in the remaining herpesviruses (HSV-2, HHV-6 and HHV-7) are also known (Fields et al., 1990, supra). Furthermore, genomic libraries are available and a large volume of plasmids encoding many different herpesvirus specific genes are available. See, generally, Fields et al., 1990, supra, and references cited therein, and B. Roizman et al., "The Human Herpesviruses," Raven Press, N.Y. (1993).

For example, plasmids are constructed which comprise DNA encoding the appropriate mutation, flanked by DNA that will undergo homologous recombination. The plasmid is cotransfected into cells, such as animal cells, with the herpesvirus DNA genome into which the mutation is to be inserted. The mutation will be inserted into this parental genome by a process of homologous recombination as the viral DNA is replicated in these cells. Progeny viruses are screened for the presence of the mutation using techniques known in the art. For example, progeny virus can be screened for their ability to replicate only in a cell line expressing a wild-type complementing copy of the mutated gene, providing the expression of the gene that is essential for virus replication. These viruses can also be screened for example, by Southern blot hybridization, Western blotting, immunofluorescence, expression of a specific mRNA species etc.

Replication defective viruses employed herein can be derived from herpesviruses, such as HSV-1, HSV-2, VZV, EBV, CMV, HHV-6 and HHV-7. Preferably, HSV-1 is employed. The virus can be rendered replication defective by effectively mutating the gene or genes encoding one or more proteins required for completing the replication cycle. The mutations can be classified nonsense (n), deletion (d) or point mutations (pm). In particular, a nonsense mutation is one where the mutated gene encodes an inactive or "nonsense" protein in place of the targeted protein. A deletion mutation is one where the gene, or a portion thereof, encoding the targeted protein is deleted. A point mutation is where one or more nucleotides is substituted such that the protein encoded therefrom is inactive. Preferably, nonsense and/or deletion mutations are employed.

The herpesvirus of the invention preferably contain one or more mutations in the ICP8 and/or ICP27 of HSV-1. Alternatively, the corresponding proteins in other herpesviruses can be mutated. Such proteins are homologous to HSV-1 ICP8 or ICP27.

In a preferred embodiment, the HSV-1 mutant is d27, HD2, d301 or n504R, most preferably d301 or n504R. The mutant d301 possesses a deletion mutation in the gene encoding ICP8 (Gao et al., J. Virol., 63:5258 (1989)). The mutant n504R possesses a nonsense mutation in the gene encoding ICP27. The particulars of the mutations are set forth below in the examples.

Viruses which encode homologous proteins to HSV-1 ICP27 include VZV, EBV, and the non-human equine herpesvirus type-1 (Davison et al., *J. Gen. Virol.*, 67:1759 (1986); Baer et al., *Nature*, 310:207 (1984); Holden et al., *J. Virol.*, 66:664 (1992)), and viruses which encode homologous proteins to HSV-1 ICP8 include VZV, EBV and CMV (Davison et al., *J. Gen. Virol.*, 67:1759 (1986); Baer et al. *Nature*, 310:207 (1984); Chee et al., *Current Topics in Microbiol. and Immunol.*, 154:125 (1990)). It is therefore possible, using the methods described above, to generate strains of these viruses which have replication defective properties similar to those described above for HSV-1 strains containing mutations in the genes encoding either ICP27 or ICP8.

As stated above, HSV-2 is known to encode many genes where the DNA sequences and protein products are homologous to those encoded by HSV-1, including those encoding ICP8 and ICP27. (Field et al., 1990, supra). The HSV-2 proteins have properties that are also very similar to their HSV-1 counterparts. See, Morse et al., *J. Virol.*, 26:389-410 (1978), and Marsden et al., *J. Virol.*, 28:624-642 (1978). Thus, replication defective strains of HSV-2 can be generated in the manner described for HSV-1. Such replication defective strains are useful as vaccines eliciting a protective immune response or immunomodulation effect against HSV-2.

An additional safety feature can be elicited in the HSV-2 mutant to reduce transformation in vivo. The HSV-2 genome contains two distinct regions of DNA that have been shown to be capable of transforming cells in tissue culture. These regions are termed mtrII and mtrIII, and their precise location on the HSV-2 genome is known (Galloway et al., *Proc. Natl. Acad. Sci. USA,* 81:4736 (1984); Ali et al., *Proc. Natl. Acad. Sci. USA,* 88:8257). In order to eliminate the possibility that vaccine strains of HSV-2 might be capable of transforming cells in vivo, these regions of DNA can be replaced by nontransforming HSV-1 sequences by homologous recombination. Replacement of such sequences is accomplished using procedures similar to those used in the generation of alterations in specific HSV-1 genes described herein.

The replication defective mutants of the invention are not limited to herpesviruses containing mutations in the ICP27 or ICP8 genes or their respective homologs. Any viral mutant which is viable, is incapable of replication and elicits a protective immune response or an immunomodulation is within the scope of the invention. For example, mutating the genes encoding the capsid proteins such that the mutant is incapable of replication are encompassed herein.

Advantageously, the herpesvirus comprises two or more mutations. Critically, at least one mutation must render the virus replication defective. Preferably, two or more of the mutations independently render the virus replication defective, such as where both the genes encoding ICP8 and ICP27 are mutated.

Examples of these viruses include, but are not limited to, strains in which a mutation in the ICP8 gene is introduced into the genome of a virus which contains an existing mutation in the ICP27 gene. Conversely, a virus strain can be constructed in which a mutation in the ICP27 gene is introduced into the genome of a virus which contains an existing mutation in the ICP8 gene. In order to replicate such viruses, a cell line is generated which is capable of expressing both the wild-type ICP27 and ICP8 genes. The procedures for the generation of cell lines which express more than one herpesvirus gene are known in the art and are similar to those described above, recognizing that transfected cells take up each of the genes included in the transfection mixture. See, generally, Quinlan et al., *Mol. Cell. Biol.* 5:957-963 (1983).

The general goal for a viral vaccine is to induce extended (even lifetime) protection from disease and to be free of both initial and long term side effects. The vaccine should induce both protective humoral antibodies and cell-mediated immunity. Live virus vaccines should be incapable of spreading from vaccinees to non-vaccinated individuals, and should not be capable of latent infection in the vaccinee.

Mutant herpesviruses described herein generally satisfy these criteria. Specifically, vaccines according to the invention should have at least the following properties: they should be viable and yet be effectively incapable of producing viable progeny virus in the host into which they are introduced; further, they should be capable of eliciting a protective immune response in that host. Included are viable herpesviruses which are incapable of replication (in the absence of an exogenous source of the protein, such as from a supporting host cell line expressing a complementing gene or genes) and are, therefore, incapable of generating progeny virus, but which is capable of expression of antigenic determinants such that a protective immune response is elicited.

Virus-specific products generally responsible for eliciting a protective immune response are proteins and glycoproteins which are expressed in the infected cell and, generally, are found on the surface of the virion. In the case of the herpesviruses, some of the major antigenic determinants are glycoproteins encoded by the viral genome. Vaccine strains of the replication defective herpesvirus can be produced which are capable of expressing either one or more proteins or glycoproteins normally expressed by an endogenous or heterologous herpesvirus or other pathogen.

According to the claimed invention, the replication defective herpesvirus can be administered to elicit a protective immune response or an immunomodulation effect against the corresponding wild-type herpesvirus. Alternatively, the replication defective herpesvirus can be further genetically engineered, in accordance with known techniques, to express a heterologous antigen or immunogen which elicits a protective immune response or an immunomodulation effect against the corresponding heterologous wild-type pathogen. The heterologous gene or genes for the antigen or immunogen can be derived from another herpesvirus, such as those enumerated above, or other infectious agents, such as viruses, bacteria, fungi or parasites.

For example, one or more genes encoding HSV-2 specific glycoproteins capable of eliciting a protective immune response can be flanked on either side with approximately 100-300 bp of HSV-1 DNA, for example, HSV-1 thymidine kinase or more preferably, glycoprotein C DNA, or any other region of the HSV-1 genome that is required for infection or replication of the virus, such as the gene encoding ICP8 or ICP27. Such a mutation simultaneously renders the herpesvirus replication defective and elicits a protective immune response against the heterologous protein. It may be beneficial to retain an intact copy of the thymidine kinase gene in a vaccine strain because the product of this gene is required for activation of many anti-HSV compounds (Fields et al., 1990, supra). This hybrid DNA is cotransfected into cells with infectious HSV-1 specific DNA which contains a mutation in either or both the ICP8 and ICP27 genes. Progeny viruses are screened for the insertion of the HSV-2 gene(s) into the specific HSV-1 locus determined by the flanking sequences as described above. These viruses can be assessed for their ability to elicit a protective immune response, as described below. Such viruses are useful in protecting individuals against both HSV-1 and HSV-2 because they are capable of expressing antigenic determinants specific for both viruses.

In another embodiment, HSV-1 glycoprotein immunogens are disclosed by Sarmiento et al., *J. Virol.*, 29:1159 (1979) ("gB"); Coker et al., *J. Virol.*, 47:172-181 (1978) ("gD"); and DeSai et al., *J. Gen. Virol.*, 69:1147-1156 (1988) ("gH"). These glycoprotein immunogens can be inserted in a mutated background, e.g., the genes encoding proteins required for replication in another herpesvirus, as described above.

As stated above, the replication defective herpesviruses described herein result in the production of increased levels of IgG2a with a consequent IgG subclass shift, preferably, similar to that induced by live virus, upon administration in vivo to a mammal.

Murine antibody responses to soluble protein and to carbohydrates are generally restricted to the IgG1 and IgG3 subclasses, respectively. Challenge of several strains of mice with a variety of live viruses have been reported to result in the preferential induction of antibodies of the IgG2a subclass. These studies have indicated that only part of the viral response is comprised of virus-specific antibodies. Thus, the effect can be viewed as virus-induced immunomodulation.

Antibody molecules differ in their abilities to bind complement and Fc receptors. The functional properties of the IgG2a subclass Ig suggest that they are important in the defense against virus infection, in which opsonization and complement-mediated lysis of viruses and destruction of virus-infected cells by antibody-dependent cellular cytotoxicity (ADCC) are important. It is also the most effective subclass for the induction of macrophages and killer cell ADCC of tumor cells, whereas IgG1 has very limited activity in ADCC.

Interferon-γ (IFN-γ) is produced by helper T cells of the Th1 subdivision. IFN-γ has diverse effects on a variety of cell types. It plays an important role in macrophage activation and has also been shown to affect polyclonal B cell activation and differentiation. IFN-γ promotes the production of IgG2a by activated murine and human B cells stimulated in IL-2 and causes human B cells treated with antibodies to Ig to enter the S phase of the cell cycle.

Tumor necrosis factor-α (TNF-α), primarily released from macrophages, has been shown to display a synergistic effect with IFN-γ in several functions (Lee et al., *J. Immunol.,* 133:1083 (1984); Stone-Wolff et al., *J. Exp. Med.,* 159:828 (1984); Williams et al., *J. Immunol.,* 130:518 (1983)), including protection against lethal infection.

Without being limited to any particular theory, HSV-infection by live or replication defective viruses preferentially activates Th1 cells; thereby, secreting IFN-γ and other cytokines. In view of the known relationships of IgG2a, IFN-γ, TNFα and ADCC, the administration of replication defective herpesviruses capable of eliciting IgG2a/IgG1 subclass shift or induces production of IFN-γ and other cytokines is useful in treating herpesvirus infections, such as herpetic stromal keratitis. Stoat et al., *J. Immunol.,* 142:760 (1989).

Replication defective herpesviruses that demonstrated the ability to induce the IgG2a/IgG1 subclass shift were those where transcription of at least some β genes occurred. Preferably, the replication defective herpesviruses is a mutated HSV-1. Most preferably, the genes encoding ICP8 and/or ICP27 have been mutated to render the herpesvirus replication defective. The mutation is preferably a nonsense or deletion mutation. Alternatively, the herpesvirus is any other herpesvirus described above where the mutation occurs in a gene permitting transcription of at least some β genes and rendering the herpesvirus replication defective. Preferably, the genes encoding the homologous proteins to HSV-1 ICP8 or ICP27, as described previously, are mutated to render the herpesvirus replication defective. In one embodiment, the herpesvirus replication defective mutant employed is not a deletion mutation to the gene encoding glycoprotein H (gH-) or ICP4.

In view of the ability of the replication defective herpesvirus of the claimed invention to increase production of IgG2a with a consequent Ig subclass shift, the mutated herpesvirus can be administered to treat immunopathologic diseases, such as herpesvirus infections in mammals; preferably, herpetic stromal keratitis or encephalitis.

Those skilled in the art will understand that dosage can be optimized using standard procedures. In general, the vaccines and pharmaceutical compositions are formulated in suitable sterilized buffer and administered (e.g., by subcutaneous, intramuscular or intradermal injection) at a dosage of between $10^3$ and $10^9$ PFU/kg. The composition can also be administered by any known means successful in eliciting the immunomodulatory response and/or protective immune response, such as oral or ocular administration in vehicles known in the art.

The following examples are provided to illustrate the invention, not to limit it. Those skilled in the art will understand that the specific constructions provided below may be changed in numerous ways, consistent with the above described invention while retaining the critical properties of the vaccine or immunomodulant.

EXEMPLIFICATION

Construction and Characterization of Viruses Encoding Mutations in the HSV-1 ICP27 Gene Cells, viruses, infections and transfections. Infection of cells with viruses and transfection of cells with DNA was carried out in Vero or V27 cells. Vero cells were obtained from the American Type Culture Collection, Rockville, Md.; the derivation of V27 cells is described below. The wild-type strain of HSV-1, KOS 1.1, was used. Cells were infected at a multiplicity of 10 pfu per cell. Disodium phosphonoacetic acid (PAA) (Abbott Laboratories, North Chicago, Ill.) was added to the medium at a concentration of 400 μg/ml as indicated below. Transfection of cells with viral DNA in marker transfer experiments was performed in V27 cells using the calcium phosphate precipitation technique (Rice et al., *J. Virol.,* 62:3814 (1988)).

The V27 cell line, which contains a stably integrated copy of the HSV-1 ICP27 gene, was isolated in the following manner. Subconfluent 100 mm diameter plates of vero cells were transfected with 0.8 μg of pSV2neo (Southern et al., *J. Mol. Appl. Genet.* 1:327 (1982)), a plasmid conferring resistance to the drug G418, and either 4 or 10 μg of pBH27 (Rice et al., *J. Virol.,* 62:3814 (1988)), a plasmid encoding HSV-1 ICP27. Two days later, the cells were passed at a ratio of 1:9 in medium containing 600 μg of G418 per ml. G418-resistant colonies were isolated 2 to 4 weeks later and grown into mass culture. The cell lines were tested for ICP27 expression on the basis of their ability to support plaque formation of the ICP27 mutants tsY46 (Sacks et al., *J. Virol.,* 55:796 (1985)) and tsLG4 (Sandri-Goldin et al., *J. Virol.,*

38:41 (1981)) at the nonpermissive temperature. Six of seventeen isolates tested positive in this assay. One of these cell lines, designated V27, was used for the isolation of ICP27 mutants. Southern blot analysis indicated that V27 cells contained approximately one copy of the ICP27 gene per haploid genome equivalent.

Generation of HSV-1 ICP27 mutants. Because ICP27 is an essential gene for the replication of HSV-1 (Sacks et al. *J. Virol.*, 55:796 (1985)), viruses containing mutations in ICP27 have a null phenotype. V27 cells were therefore used to propagate such mutants.

Insertion of the *E. coli* lacZ gene into the HSV-1 chromosome is a useful tool for the isolation of viral mutants (Carmichael et al., *J. Virol.*, 63:591 (1989); Goldstein et al., *J. Virol.*, 62:196 (1988)). Viral plaques expressing β-galactosidase, the product of the lacZ gene, can be identified on the basis of their color (blue) in the presence of x-gal, a chromogenic substrate for β-galactosidase. As described in detail below, an HSV-1 mutant expressing β-galactosidase was first isolated which contains an in-frame insertion of the lacZ gene into the ICP27 coding sequences. This virus then served as a recipient in marker transfer experiments for the introduction of specifically mutated ICP27 alleles into the viral genome. Recombinants containing the newly introduced ICP27 genes were identified as clear plaques against a background of parental blue plaques.

Figure 4A:
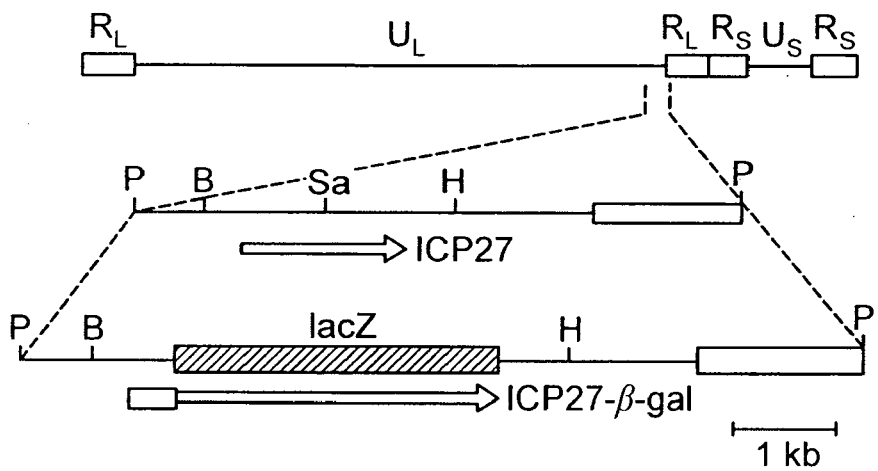
FIG. 4 is a diagrammatic representation of the location and structure of wild-type and mutant HSV-1 ICP27 genes. (A) Structures of the wild-type and the lacZ insertion mutant genes. A representation of the prototype arrangement of the HSV-1 genome is shown at the top. A PstI restriction fragment from the wild-type and the d27-lacZ1 gene is shown below. The narrow lines denote unique (U) regions of the viral genome, the open bars denote repeat regions (R), and the hatched bar denotes the E. coli lacZ sequence. The upper arrow represents the coding sequences for the 63 kDa ICP27 protein and the bottom arrow represents the coding sequences for the approximately 137 kDa ICP27-β-galactosidase fusion protein. (B) Structures of the wild-type, nonsense and deletion mutant genes. ICP27 mutant genes were constructed by deleting restriction fragments (parentheses) or inserting XbaI or NheI oligonucleotide linkers (X and N, respectively) containing stop codons in all three reading frames. The arrows represent either the wild-type ICP27 protein (top) or the truncated forms of ICP27 encoded by the nonsense mutants. Restriction sites: P, PstI; B, BamHI; Sa, SalI; H HpaI; R, RsrII; St, StuI; Ss, SspI; X, XbaI; N, NheI.

In order to make the HSV-1 lacZ insertion mutant, a recombinant plasmid was constructed in which the lacZ coding region was inserted into a deleted version of the ICP27 gene. This fusion gene was then cotransfected into V27 cells with infectious HSV-1 DNA. When the progeny viruses from this transfected culture were plated onto V27 cells in the presence of X-gal, approximately 3% of the plaques were blue. A blue plaque was picked, and the resulting virus clone was designated d27-lacZ1. Southern blot analysis indicated that d27-lacZ1 has a genomic structure consistent with the replacement of the WT ICP27 gene with the ICP27-lacZ fusion gene (FIG. 4A). In addition, d27-lacZ1-infected cells did not express the WT ICP27 but instead expressed a polypeptide of approximately 137 kDa, consistent with the size predicted for the ICP27-β-galactosidase fusion protein. The stock of d27-lacZ1 virus was unable to form plaques on Vero cells ($<2 \times 10^3$ pfu/ml) but formed plaques efficiently on V27 cells ($2 \times 10^8$ pfu/ml). The experimental details for the isolation of d27-lacZ1 are now described below.

The plasmid pPs27pd1 (Rice et al., *J. Virol.*, 63:3399 (1989)) contains a 6.1-kilobase (kb) PstI insert derived from HSV-1 genome DNA. This fragment contains the entire ICP27 gene, as well as adjoining sequences (FIG. 4A). Derivatives of pPs27pd1 which contain a deletion in the ICP27 gene and insertion of the lacZ gene were constructed in the following manner. pPs27pd1 was linearized in the ICP27 coding region by digestion with SalI. The DNA was then treated with Bal 31 such that approximately 0.5 kb of DNA was removed from each end. The ends were repaired by a fill-in reaction using the Klenow fragment of *E. coli* DNA polymerase (Ausubel et al., *Current Protocols in Molecular Biology*, John Wiley and Sons, NY (1987)). This DNA was ligated to BglII linkers (New England BioLabs, Inc., Beverly, Mass.) and the product was digested with BglII, religated, and used to transform *E. coli*. Four plasmid isolates were obtained each of which contained the lacZ gene inserted in the same orientation as the ICP27 gene.

Each of the four plasmid DNAs was digested with PstI, individually mixed with WT HSV-1 DNA, and transfected into V27 cells. After 4 days, the cultures were harvested and the resulting virus stocks were plated onto V27 cells under a liquid overlay of medium 199 (GIBCO Laboratories, Grand Island, N.Y.) containing 1% newborn calf serum and 0.1% human immunoglobulin. After 2 days, the medium was replaced with medium 199 containing 1% newborn calf serum, 0.5% agarose, and 300 µg of 5-bromo-4-chloro-3-indolyl-β-Dgalactopyranoside (X-gal; Boehringer Mannheim Biochemicals, Indianapolis, Ind.) per ml. One of the resulting four stocks of virus gave rise to a high percentage (approximately 3%) of blue plaques. One blue plaque was purified three times, and the resulting virus clone was designated d27-lacZ1. Southern blot analysis of d27-lacZ1 DNA indicated that the WT ICP27 gene had been replaced with the ICP27-lacZ fusion gene (FIG. 4A). In addition, Southern blot analysis of viral DNA, as well as restriction analysis of the parental plasmid (designated pPsd27-lacZ1), indicated that approximately 0.8 kb had been deleted from the ICP27 gene in d27-lacZ1.

Construction of HSV-I mutants containing deletion or nonsense mutations in the ICP¢gene. Five plasmids were generated which contained deletions or nonsense codon insertions in the ICP27 gene, as generally described in Knipe et al., *J. Virol.*, 63:3400, et seq. See FIG. 4B. Viral DNA inserts in each plasmid were separated from vector sequences and were cotransfected into V27 cells with d27lacZ1 DNA. Resulting progeny viruses were plated on V27 cells in the presence of X-gal, and a fraction (approximately 1 to 5%) formed clear plaques. Viruses which formed clear plagues were isolated and screened for the presence of the newly introduced ICP27 alleles in an immunofluorescence assay or by DNA restriction analysis as described below. For each mutant, a positive plaque was purified three times. A potential ICP27 deletion mutant was designated d27-1. Potential nonsense mutants were designated n59R, n263R, and n504R; the numbers in the names of the mutants correspond to the number of amino-terminal ICP27 residues expected to be present in each truncated protein. For comparison, the wild-type protein consists of 512 amino acid residues.

The recombinant viral genomes were characterized by Southern blot hybridization to confirm that each virus contained the appropriate mutation. Viral DNA was isolated from infected V27 cells and the PstI and XbaI restriction enzyme patterns were examined in Southern blots. A 6.1 kb PstI HSV-1 DNA fragment containing the wild-type ICP27 gene was used as a probe. Because this fragment includes some of the repeat sequences in the L component of the HSV-1 genome (FIG. 4A), two bands were evident when wild-type HSV-1 DNA was examined. These were the 6.1 kb ICP27 fragment and a 3.3 kb fragment which was derived from the other $U_L$-$R_L$ junction. In contrast, all five ICP27 mutant DNAs lacked the 6.1 kb fragment but contained the 3.3 kb fragment. The mutant d27-1 contained a new fragment of DNA of approximately 4.6 kb, consistent with its expected 1.6 kb deletion. The four remaining mutants each contained two new bands, the combined sizes of which approximated 6.1 kb, consistent with the insertion of an XbaI site at the appropriate position in each mutant genome. Furthermore, none of the mutant genomes contained the 8.4 kb PstI fragment, which should only be present in the parental d27-lacZ1 DNA.

Plaque assays were performed to determine whether the mutants were capable of growth in Vero cells. All five mutants were unable to form plaques on Vero cells at the lowest dilution which could be tested (Table 1) (lower dilutions destroyed the cell monolayer). However, each mutant formed plaques efficiently on V27 cells. Because the only known intact HSV-1 gene resident in the V27 genome is a wild-type copy of the ICP27 gene, these results indicate that the lethal defect in each mutant is complemented in trans by this wild-type form of ICP27.

TABLE 1

Growth of HSV-1 ICP27 mutants[a]

| Virus | Viral titer (pfu/mt) | |
|---|---|---|
| | Vero cells | V27 cells |
| KOS1.1 (wt) | $7 \times 10^8$ | $5 \times 10^8$ |
| D27-1 | $<2 \times 10^3$ | $3 \times 10^8$ |
| n59R | $<2 \times 10^3$ | $3 \times 10^8$ |
| n263R | $<2 \times 10^3$ | $3 \times 10^8$ |
| n406R | $<2 \times 10^3$ | $3 \times 10^8$ |
| n504R | $<2 \times 10^3$ | $3 \times 10^8$ |

[a]Viral stocks were titrated by plaque assay on the cell lines indicated

The experimental details for the isolation of these mutants is now described below.

Figure 4B:
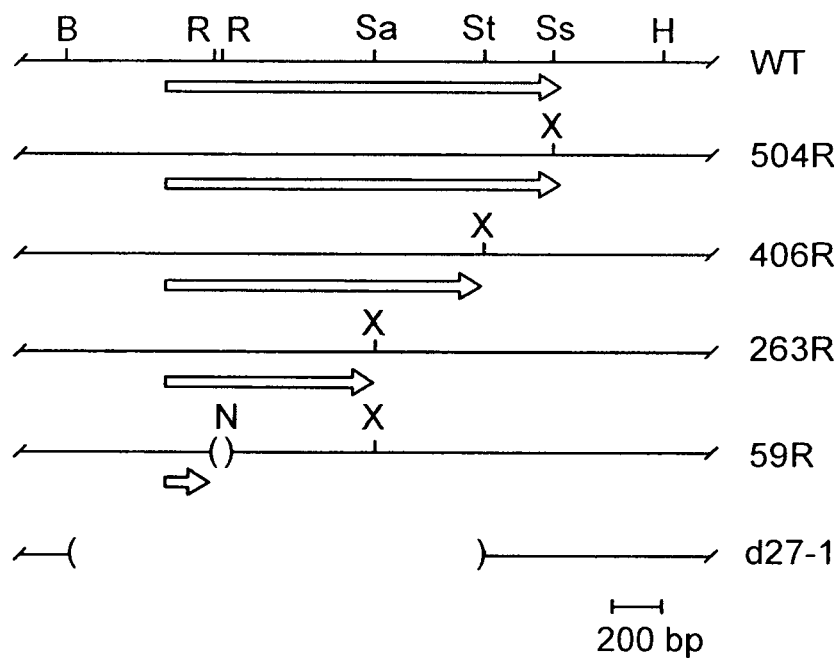

Deletion and nonsense mutations in the ICP27 gene were engineered into the plasmid pPs27pd1 (FIG. 4B). The plasmids containing the 406R and 504R mutations, pPs-406R and pPs-504R respectively, were constructed as described in Rice et al., *J. Virol.*, 63:3399 (1989). The plasmid pPsd27-1 was constructed by digesting pPs27pD1 with BamHI and StuI, filling in the 3' recessed BamHI DNA ends using this Klenow fragment of *E. coli* DNA polymerase, and recircularizing the large DNA fragment with DNA ligase. The plasmids pPs-59R and pPs-263R were constructed by substituting the mutant 2.4 kb BamHI-SstI fragments from the plasmids pBH-59R and pBH-263R described above for the WT 2.4 kb BamHI-SstI fragment of pPs27pd1.

Recombinant viruses were constructed as follows. The plasmid DNAs described above were digested with PstI, individually mixed with d27-lacZ1 viral DNA, and transfected into V27 cells. Progeny viruses were harvested 3 to 5 days later and were plated on V27 cells in the presence of X-gal, as described above. Clear plaques, which were observed at frequencies of 0.5 to 5%, were picked and screened to determine whether they had acquired the ICP27 gene mutations.

Plaque isolates were screened in two ways. Plaque isolates d27-1, n59R, and n263R were purified three times in V27 cells and then used to infect V27 cells. Crude viral DNA was prepared from the infected cells (Gao et al., *J. Virol.*, 63:5258 (1989)). The XbaI and BamHI restriction enzyme patterns of each DNA sample were examined in order to confirm the presence of each mutation. In the case of n406R and n504R, initial plaque isolates were used to prepare small virus stocks. Vero cells grown on glass cover slips were then infected with each virus. The infected cells were fixed and stained for immunofluorescence using an anti-ICP27 monoclonal antibody, (Ackerman et al., *J. Virol.*, 52:108 (1984)). Isolates of n406R and n504R were then plaque purified two more times and large stocks of each mutant were prepared in V27 cells.

Expression and intracellular localization of mutated ICP27 polypeptides. The mutants were next examined for expression of ICP27-related polypeptides. Vero cells were either mock-infected or infected with each virus, and cell extracts were prepared at 10 hour PI. Proteins were separated by SDS-PAGE, transferred to nitrocellulose, and reacted with the monoclonal antibody H1113. No ICP27-related polypeptides were detected in extracts of mock-, d27-1-, or n59R-infected cells. An approximately 38 kDa protein was detected in the extracts of n263-infected cells, and an approximately 52 kDa protein was detected in the extracts of n406-infected cells. Cells infected with n504R produced an ICP27-related polypeptide which comigrated with the 63 kDa wild-type protein. The sizes of the truncated proteins were in rough agreement with the predicted sizes based on the DNA sequence of the ICP27 gene (McGeoch et al., *J. Gen. Virol.*, 69:1531 (1988)).

To determine the intracellular distribution of the mutant proteins expressed on the viral genome, Vero cells infected with each mutant were harvested at 4 h PI, and were fixed and processed for immunofluorescence microscopy using the monoclonal antibody H1113. Cells infected with the wild-type virus exhibited localized nuclear staining wherein one or more areas stained more intensely. These areas did not correspond to any particular nuclear regions such as nucleoli. No staining above background levels was detected in cells infected with d27-1 or n59R. Cells infected with n263R exhibited nuclear staining and, similar to virus-infected cells, some areas of the nucleus stained more intensely. These areas appeared to correspond to nucleoli. Cells infected with n406R also exhibited nuclear staining, but the pattern of staining differed from that in wild-type virus-infected cells in two respects. First, in most cells the n406R encoded ICP27 protein was largely excluded from the nucleolar regions. Second, many n406R-infected cells exhibited a rather punctate pattern of staining, wherein the mutated protein was concentrated in globular clusters in the nucleus. Cells infected with n504R also exhibited nuclear staining, but in this case, the protein appeared to be present throughout the nucleus exhibiting a more diffuse pattern than that seen in wild-type virus infected cells. These results indicate that mutated forms of ICP27 encoded by n263R, n406R and n504R efficiently localized to the cell nucleus but differed from each other and from that of wild-type virus in their patterns of intranuclear accumulation.

Viral DNA synthesis in cells infected with ICP27 mutants.

The phenotype of the ICP27 mutants with regard to viral DNA replication was next determined. To determine the viral DNA synthesis phenotype of each mutant, Vero cells were mock-infected or infected with each of the mutants. After a 1 hour adsorption period, the monolayers were washed extensively with warm medium to remove unadsorbed virus. Total DNA was prepared by the method of Challberg, *Proc. Natl. Acad. Sci. USA*, 83:9094 (1986) at either 1 or 16 hour PI. Purified DNA was quantitated by UV absorption at 260 nm. The DNA was diluted and denatured in 100 mM sodium hydroxide for 30 minutes at room temperature. An equal volume of 12×SSC (1×SSC is 0.15 M sodium chloride plus 0.015 M sodium citrate) was added, and the DNA was applied to a nitrocellulose filter using a slot-blot manifold (Schleicher & Schuell, Keene, N.H.). The filters were baked and the DNA was hybridized to $^{32}$P-labeled HSV-1-specific probes prepared by random primer labeling. Probes included either pSHZ, containing the ICP0 gene (Nabel et al., 1988, supra), or pRB3441, containing the gene for Vmw65 (McKnight et al., *Cancer Cells*, 4:163 (1986)). An HSV-1 mutant, d102, which contains a large deletion in the ICP8 gene and is therefore unable to replicate its DNA (Gao et al., *J. Virol.*, 63:5258 (1989)), was included in these experiments as a negative control. Viral DNA replicated to high levels in wild-type virus-infected cells. In contrast, no evidence of viral DNA replication could be detected in d102-infected cells. All five ICP27 mutants were capable of replicating viral DNA during the course of the infection.

To quantitate these results, the amount of radioactivity hybridizing to each slot was measured by scintillation counting and the data are summarized in Table 2. Based on these results, the mutants could be divided into two phenotypic classes with respect to DNA replication. The first class containing mutants d27-1, n59R, n263R, and n406R, exhibited a partial defect in viral DNA amplification (6 to 38% of the wild-type level). The second class, consisting only of n504R, exhibited a wild-type phenotype for viral DNA replication. It is important to note that these experiments measured the level of viral DNA accumulation in infected cells, a quantity determined by the rate of DNA synthesis as well as by the stability of the replicated DNA.

TABLE 2

Viral DNA replication in cells infected with ICP27 mutants

| Virus | DNA amplification[a] in: | | % of wild-type amplification[b] in: | |
|---|---|---|---|---|
| | Expt. 1 | Expt. 2 | Expt. 1 | Expt. 2 |
| KOS1.1 (wt) | 80 | 142 | 100 | 100 |
| d102 | 0.5 | 0.4 | | |
| d27-1 | 18 | 11 | 23 | 8 |
| n59R | 15 | 22 | 19 | 15 |
| n263R | 17 | 9 | 21 | 6 |
| n406 | 30 | 23 | 38 | 16 |
| n504 | 98 | 121 | 123 | 85 |

[a]The numbers shown are the ratio of the amount of HSV-1 DNA in infected Vero cells at 16 h PI to the amount present at 1 h PI. The DNA was detected and quantitated as described above. The probe in experiment 1 was pSHZ, and the probe in experiment 2 was pRB3441.
[b]The amount of DNA amplification by the wild-type virus in each experiment was normalized to 100%, and the other values are expressed relative to this value. Because d102 exhibited a decrease in the amount of DNA during infection, a percent value was not determined.

Patterns of viral protein synthesis in ICP27 mutant infected cells. To analyze the effect of mutations in the ICP27 gene on viral gene expression, viral protein synthesis was examined in mutant infected cells. Mock- or HSV-1-infected Vero cells were labeled with 15 μCi [$^{35}$S]-methionine/ml of medium at 3, 6, or 9 h PI. Proteins were extracted from the cell, separated by SDS-PAGE and visualized by autoradiography. At 3 and 6 hours PI, with the exception of n406R, the ICP27 mutants exhibited patterns of protein synthesis that were qualitatively similar to the pattern in wild-type virus infected cells. Cells infected with n406R appeared to lack several proteins, including ICP6, ICP8, and the precursor to gB (pgB). However, at 9 hours PI, cells infected with all five ICP27 mutants exhibited both quantitative and qualitative differences in viral protein synthesis compared with wild-type virus. The five mutants could be divided into four phenotypic classes with respect to viral protein synthesis at 9 hours PI. Mutants d27-1 and n59R were reproducibly indistinguishable from each other in terms of their patterns of protein synthesis. Both of these mutants expressed high levels of most β-proteins but expressed lower levels (relative to wild-type levels), of several γ-1 proteins, including ICP5 and ICP25, 9 hours PI. Mutant n263R exhibited a pattern of protein synthesis at 9 hours PI that was very similar to that of d27-1 and n59R, but this mutant expressed slightly more of several γ-1 proteins. Mutant n406R had an unusual phenotype with regard to viral protein synthesis in that greatly reduced levels of many viral proteins including ICP6, ICP8, and pgB were evident in cells infected with this mutant. This effect did not extend to all viral proteins in that higher levels of the γ-1 proteins, ICP5 and ICP25, were evident at 9 hours PI compared with d27-1-infected cells. Mutant n504R expressed high levels of β and γ-1 proteins, such as ICP1/2 and ICP15.

In wild-type virus infected cells at 9 hours PI, the expression of the α proteins ICP4 and ICP27, was reduced markedly. This was not the case when cells were infected with any of the five ICP27 mutants. In addition, n504R-infected cells failed to turn off expression of the ICP27 polypeptide (because none of the other mutants encodes a protein that comigrates with WT ICP27, this was the only case in which a direct comparison of ICP27 protein synthesis rates was possible). With the exception of n406R, the ICP27 mutants also exhibited a defect in their ability to negatively modulate the expression of many β proteins, including ICP6 and ICP8. These results suggest that ICP27 has a negative regulatory effect on the expression of α and β genes.

To determine whether the defect in viral protein synthesis observed in cells infected with mutant viruses could be corrected by expression of the wild-type form of the protein, the following experiment was performed. Vero or V27 cells were infected in parallel with wild-type virus or with one of the mutants. Infected cell proteins were labeled with [35S]-methionine at 15 h PI and were subsequently analyzed by SDS-PAGE and autoradiography. The pattern of protein expression of each mutant observed at 15 hours PI in Vero cells was similar to that described above for 9 hours PI. However, when V27 cells were infected with each of the mutants, a pattern of protein synthesis more similar to that of the wild-type virus was evident.

Accumulation of viral mRNA in ICP27 mutant virus infected cells. Steady-state levels of viral mRNAs expressed in mutant infected cells were analyzed by Northern blot hybridization. RNA was isolated from cells infected with each mutant by treating the cells with Nonidet P-40 and was then extracted with phenol-chloroform. It was precipitated in ethanol (Klessig et al., *J. Virol.*, 16:1850 (1975)), suspended in buffer, digested with RNase-free DNase I (Bethesda Research Laboratories, Gaithersburg, Md.), extracted with phenol-chloroform and then reprecipitated in ethanol. Ten micrograms of each RNA sample was subjected to electrophoresis through denaturing formaldehyde-agarose gels (Sambrook et al., Supra). Following electrophoresis, the RNA was transferred to GeneScreen filters (DuPont, NEN Research Products, Boston, Mass.). Hybridization of the RNA to $^{32}$P-labeled probes, was then performed (Rice et al., *J. Virol.*, 49:35 (1984)). The probes included pBH27 (encoding the ICP27 gene (Rice et al., supra), pK1-2 (encoding the ICP4 gene (DeLuca et al., *Nucl. Acids Res.*, 15:3391 (1987)), and pEcoRI-BamHI-I-I (encoding the gC gene (Frink et al., *J. Virol.*, 45:634 (1983)). Autoradiograms were analyzed densitrometrically in an Ultrascan laser densitometer and online integrator (LKB Instruments, Inc., Rockville, Md.).

Specifically, RNA was extracted from Vero cells which were mock-infected, infected with wild-type virus or with the mutants n59R, d27-1, or n504R. Wild-type virus infections were carried out in the presence or absence of PAA, a specific inhibitor of HSV-1 viral DNA synthesis. Cytoplasmic RNA was isolated from the infected cells at 9 hours PI. Following Northern blot transfer, filters were probed with radiolabeled DNAs specific for ICP27, ICP4, or gC mRNA. No ICP27-specific mRNA was evident in mock- or d27-1-infected cells. RNA isolated from n59R- or n504R-infected cells contained two- to threefold more 2.0 kb ICP27 mRNA than did RNA obtained from wild-type virus-infected cells.

This result was qualitatively consistent with the elevated levels of ICP27 protein synthesis observed at 9 h PI in n504R-infected cells.

In contrast to the results obtained with the ICP27-specific mRNA, approximately equal amounts of ICP4 mRNA were observed in d27-1-, n59R-, and wild-type virus-infected cells, whereas n504R-infected cells accumulated only 1.6-fold more ICP4 mRNA than did wild-type virus-infected cells. These results were somewhat unexpected because little or no ICP4 protein was evident at 9 hours PI in wild-type virus-infected cells. The synthesis of ICP4 was readily detected in cells infected with the ICP27 mutants. Therefore, the level of expression of ICP4 at 9 hours PI does not reflect the level of cytoplasmic ICP4 transcripts. This suggests that ICP4 mRNA is translated more efficiently in cells infected with ICP27 mutants than in cells infected with wild-type virus.

The accumulation of mRNA specific for the γ-2 gene encoding gC was examined in cells infected with the mutants. Inhibition of viral DNA replication by PAA drastically reduced the amount of gC mRNA which accumulated in cells infected with wild-type virus (gC mRNA could be detected in lane 1' upon longer exposures of the autoradiogram). Neither d27-1-, n59R-, nor n504R-infected cells expressed detectable levels of gC mRNA. This is of particular interest in the case of the mutant n504R, which replicated WT levels of DNA during infection. Expression of γ-2 genes requires both the replication of the viral DNA and a virus-encoded transacting factor, namely ICP27.

Construction and Characterization of Mutants in the HSV-1 ICP8 Gene

Isolation of ICP8 expressing cell lines. Vero cells were transformed with the plasmid pSG18-SacI (Lee et al., *J. Virol.*, 46:909 (1983); Quinlan et al., *Mol. Cell. Biol.*, 5:957 (1985)) or p8B-S (Gao et al., *Virology*, 163:319 (1988)) and pSVneo (Southern et al., *J. Mol. Appl. Genet.*, 1:327 (1988)) essentially as described by DeLuca et al., (DeLuca et al., *J. Virol.*, 56:558 (1985)). After growth in medium containing the antibiotic G418, 21 drug-resistant colonies were isolated, amplified and screened for their ability to complement the growth of the ICP8 mutants ts13, ts18, and tsHA1 (Conley et al., *J. Virol.*, 37:413 (1981); Holland et al., *J. Virol.*, 49:947 (1984)). At the nonpermissive temperature, these ts mutants formed plaques in 7 of 21 cell lines derived from cultures receiving the ICP8 gene but they did not form plaques in Neo[r] cells which were derived from cells that were transfected with pSV2neo alone. Cell lines, B10 and S2, derived from a cells transfected with plasmids p8B-S and pSG18-SacI respectively, yielded the highest levels of complementation and were chosen for further study (Table 3). Wild-type virus formed plaques in Neo[r] cells as well as in B10 and S2 cells at both temperatures. The mutant viruses ts13, ts18 and tsHA1 formed plaques efficiently only at 33.5° C. in Neo[r] cells but formed plaques at an efficiency equal to that of wild-type at both temperatures in B10 and S2 cells. Southern blot hybridization was performed to determine the copy number of the ICP8 gene in these cell lines, and B10 and S2 cells contained approximately 1 and 10 copies per haploid genome, respectively.

TABLE 3

Complementation of ICP8 mutants by B10 and S2 Cells[a]
Titer (10⁹ pfu/mlO[b])

| | B10 | | S2 | | Neo[r] | |
|---|---|---|---|---|---|---|
| Virus | 33.5° C. | 39° C. | 33.5° C. | 39° C. | 33.5° C. | 39° C. |
| KOS1.1 | 1.7 | 1.7 | 0.7 | 2.0 | 1.3 | 1.8 |
| ts13 | 4.3 | 3.1 | 2.3 | 4.0 | 1.0 | <0.001 |
| ts18 | 3.0 | 3.2 | 2.3 | 2.7 | 1.7 | <0.001 |
| tsHA1 | 2.3 | 3.7 | 3.7 | 1.7 | 2.4 | <0.001 |

[a]Cultures of B10, S2, and Neo[r] cells were infected with each virus and incubated at 33.5° C. or 39° C.
[b]plaque numbers were counted for 2 to 3 days.

Figure 5:
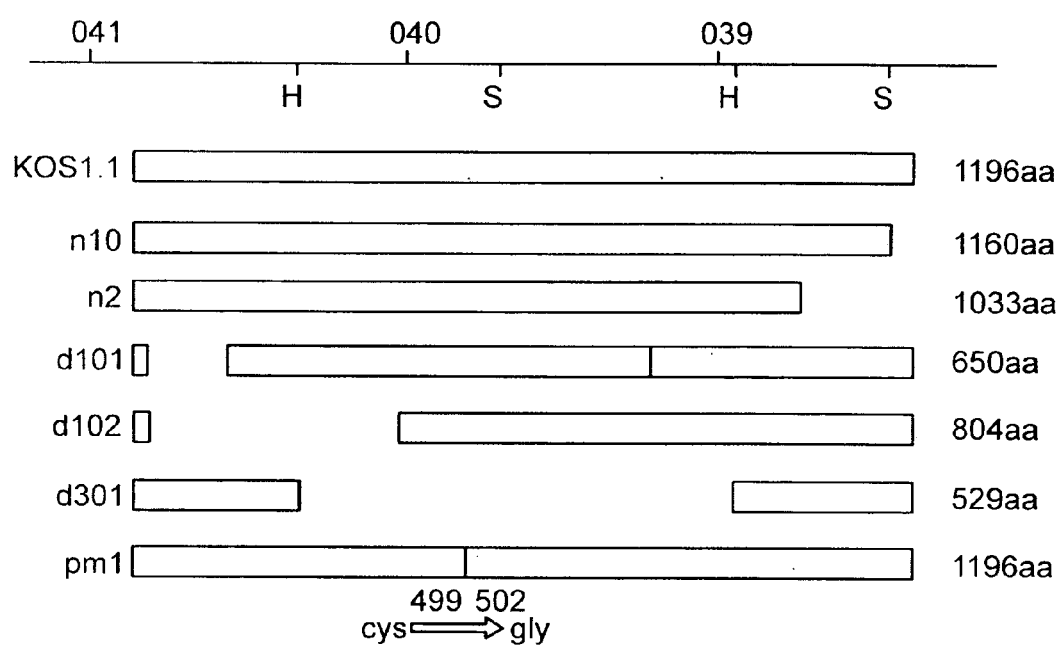
FIG. 5 is a diagrammatic representation of the locations of the ICP8 nonsense (n), deletion (d) and point (pm) mutations. The location of the ICP8 coding region on the HSV-1 genome is shown at the top of the figure. The restriction sites shown are BamHI (B), NotI (N) and SalI (S).

Plasmids. The plasmids p8-S, pSV8 and pm1 and their nucleotide numbering system are described (Gao et al., *Virology*, 163:319 (1988); Su et al., *J. Virol.*, 61:615 (1987)). The plasmid p8B-S was constructed by cloning a 5.9 kb BamHI-SacI fragment (map units 0.374 to 0.411), including the ICP8 promoter, into pUC18. The plasmid pSV8 was constructed by inserting a 5.5 kb SmaI-SacI fragment (map units 0.374 to 0.409) downstream of the simian virus 40 early promoter. The plasmid pm1 was derived from plasmid pSV8 by changing codons 499 and 502 of the ICP8 gene such that they encode cysteine rather than glycine. Mutant ICP8 plasmids used in this study were derived from pICP8 or pSPICP8, in which a 5.5 kb SmaI-SacI fragment (map units 0.374 to 0.409) was inserted into pUC19 or pSP64, respectively. Plasmids pn10 and pn2 were generated by linearization of the plasmid spICP8 (which was achieved by partial digestion with SmaI) and subsequent insertion of a 14 nucleotide XbaI linker (Gao et al., 1988, supra; New England BioLabs, Inc., Beverly, Mass.) containing stop codons in all three reading frames at nucleotides 4084 and 3695, respectively. Therefore, pn10 encodes the first 1,160 amino acid residues, and pn2 encodes the first 1,029 amino acid residues of ICP8 as well as 4 additional amino acids, encoded by the XbaI linker sequence. See FIG. 5. Plasmid pd301 was generated by an internal in-frame deletion of a 2,001-base-pair (bp) NotI fragment (nucleotides 1395 to 3396). Plasmids pd101 and pd102 were constructed as follows: the plasmid pSPICP8 was linearized by partial digestion with SmaI, and a 12 nucleotide BglII linker (Gao et al., 1988, supra, was ligated to it. A 1,642-bp deletion was generated by digestion with BglII (converted from a SmaI site at nucleotide 652) and BamHI (nucleotide 2294) to yield plasmid pd101. Thus, pd101 lacks codons for residues 17 to 563 but has an insertion of one Arg codon encoded by the BglII linker sequence. A 1,188 bp deletion was generated by digestion with BglII (converted from SmaI at nucleotides 652 and 1840) to yield plasmid pd102. Thus, pd102 lacks codons for residues 17 to 411 of the ICP8 coding sequence but encodes three additional amino acids, Arg-Ser-Ser, in the BglII linker sequence. Both plasmids pd101 and pd102 also contain a 14 nucleotide XbaI linker at nucleotide 4419, downstream of the ICP8 poly(A) signal. Because there are other SmaI sites around nucleotides 4084 and 1840, both pn10 and pd102 were sequenced to determine the exact mutation sites. See FIG. 5.

Construction of mutant viruses. To examine the functional domains of ICP8, several different types of mutations were introduced into the coding region of the ICP8 gene (FIG. 12): (i) nonsense mutations (pn10 and pn2); (ii) internal deletions (pd301, pd101, and pd102); and (iii) a site specific mutation (pm1) (Gao et al., *Virology*, 163:319 (1988)). To facilitate screening for recombinant viruses after marker transfer, a mutant virus containing a lacZ gene inserted into the ICP8 coding region was constructed in a manner similar to that described above for the generation of ICP27 mutants. This recombinant virus, designated as HD-2, formed blue plaques in the ICP8-expressing cell lines in the presence of X-Gal, but did not form any plaques in Vero cells. DNA encoding the various mutant forms of ICP8 was recombined into this parental strain, and the resulting progeny were isolated from white plaques. White plaques appeared at frequencies ranging from 2 to 39%. The frequency of white plaques in cells transfected with HD-2 DNA and pd101 or pd102 was not above the background. This was probably due to the limited amount of viral sequences available for recombination between pd101 or pd102 and HD-2 DNA.

The following types of analyses were performed to verify that the recombinant viruses contained the appropriate mutation in the ICP8 gene. Viral DNA was isolated, digested with appropriate restriction enzymes, and analyzed by agarose gel electrophoresis. Southern blot analysis was performed to confirm the presence of mutations in viral DNA and to determine the purity of the mutant virus populations. For example, the 8.2 kb BamHI G fragment of wild-type DNA was divided into 6.8- and 1.4 kb fragments in n2 DNA by digestion with BamHI and XbaI due to the presence of the XbaI linker. The junction region of BamHI G and V (2.3 kbp) was replaced by the lacZ gene in HD-2; therefore, digestion of HD-2 DNA with BamHI and XbaI generated a 12.6 kb fragment. Comparison of KpnI digested wild-type, HD-2, and n2 DNAs revealed that wild-type and n2 DNAs were similar to each other but differed from that of HD-2 DNA due to the lacI insertion.

The experimental details for the isolation of viruses containing mutations in the ICP8 gene are now described below.

The mutant virus HD-2, containing a lacZ insertion in the ICP8 gene, was isolated as follows. After deletion of a 780-bp XhoI fragment from pICP8, this plasmid was briefly digested with Bal 31, a BglII linker was added to the ends of the DNA, and the lacZ gene (Pharmacia, Inc., Piscataway, N.J.) was inserted. The lacZ gene of pMC1871 contains no transcriptional promoter and also lacks the first eight non-essential amino-terminal codons. The mixture of ICP8:lacZ plasmids was transfected into B10 cells along with wild-type viral DNA. Progeny virus were isolated and were plated on B10 or S2 cells in medium 199 and 1% calf serum containing 0.1% human immune serum for 1 to 2 days at 37° C. To detect β-galactosidase activity, the medium was then changed to medium 199 plus 1.0% agarose containing 400 μg of 5-bromo-4-chloro-3-indolyl-D-galactopyranoside (X-Gal) per ml, and incubation was continued for 8 to 16 hours. Recombinant viruses were identified as blue plaques and were isolated at a frequency of approximately 0.1 to 0.5%. One mutant isolate, termed HD-2 was plaque purified.

HD-2 served as the parental virus for the generation of all the mutant viruses in this study except for d301. After cotransfection of infectious HD-2 DNA with plasmids encoding a mutated ICP8 gene, recombinant viruses were isolated from white plaques propagated in the presence of X-Gal.

Figure 12:
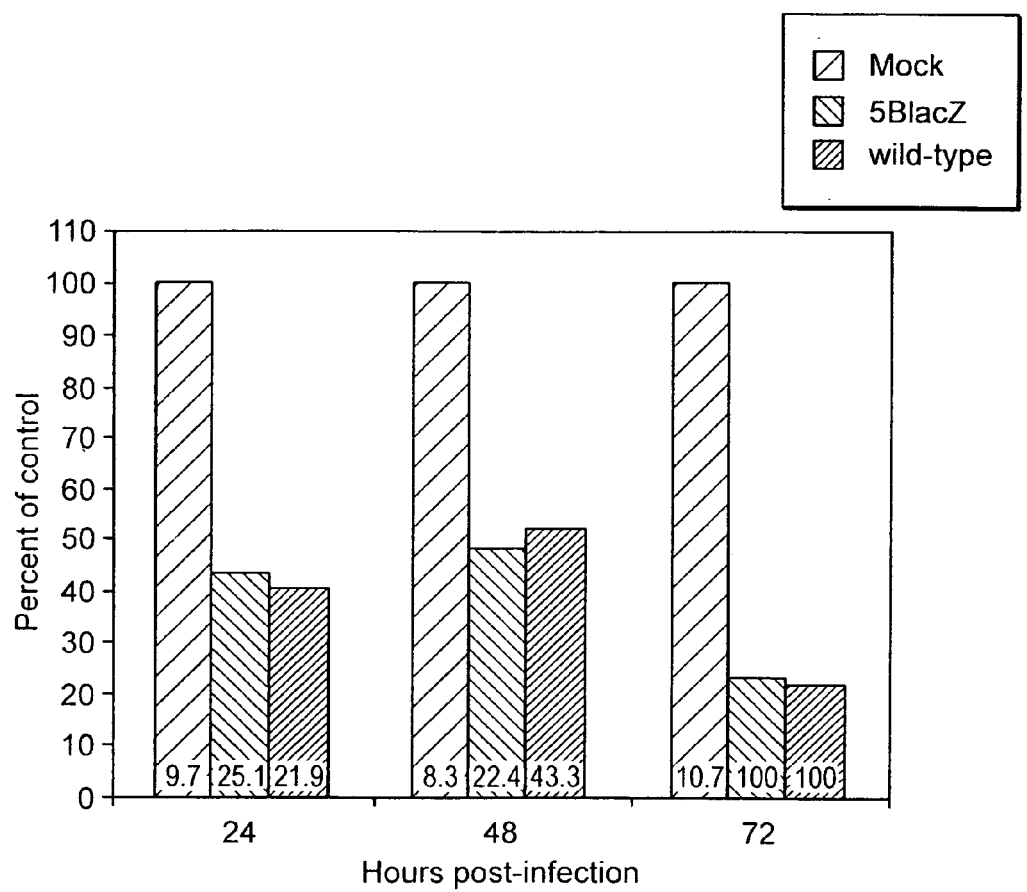
FIG. 12 is a graphic illustration of the effect of virus infection on the killing of Vero cells examined at various times post-infection. The columns represent total cell counts (both live and dead cells) expressed as a percentage of mock-infected control. The wild-type virus is strain 186 syn$^+$-1. Numbers within each bar represent the amount of dead cells (determined by uptake of trypan blue dye) expressed as a percentage of the total cell count for the particular data point; each data point represents an average of two values.

The mutant virus d301 was constructed by cotransfection of B10 cells with infectious wild-type viral DNA and the plasmid pd301, in which a 2,001 bp NotI fragment was deleted from the ICP8 coding sequence (FIG. 12). Progeny virus from this transfection were tested for their replicated in B10 cells but not in Vero cells. Growth properties of mutant viruses. Each of the mutant viruses presented in FIG. 12 was unable to replicate in Vero cells and required complementation by the wild-type copy of the ICP8 gene present in B10 or S2 cells. Each of the mutant viruses replicated to levels similar to wild-type levels in these ICP8-expressing cell lines. The sizes of the plaques produced by the mutant viruses were slightly smaller than those produced by wild-type virus. Furthermore, in all cases, the mutant viruses maintained their mutant phenotype when propagated in either B10 or S2 cells.

Expression of ICP8 by mutant viruses. Viral protein synthesis was examined in mutant infected cells by western blotting as described above. The rabbit polyclonal serum 3-83 (Knipe et al., *J. Virol.*, 61:276 (1987)) or the mouse monoclonal antibody 10E-3 (Rose et al., *J. Gen. Virol.*, 67:1315 (1986)) was used to detect ICP8. The sizes of the ICP8 polypeptides specified by the mutant viruses were consistent with the predicted sizes. The mouse monoclonal antibody 10E-3 reacted with ICP8 polypeptides expressed by mutants pm1, d101, d102, and d301, but not with those expressed by n10 and n2 (Table 4) suggesting that this antibody reacts with an epitope contained, at least in part, within the carboxyl-terminal 36 amino acids of ICP8. These results also indicate that d101, d102, and d301 contain in-frame deletions.

TABLE 4

Solubility of ICP8 encoded by viral mutants

| | % of ICP8 | | |
|---|---|---|---|
| Virus | Supernatant[a] | Pellet | Antibody[b] |
| KOS1.1 | 81 | 19 | 10E-3 |
| pm1 | 12 | 88 | 10E-3 |
| d101 | 22 | 78 | 10E-3 |
| d102 | 33 | 77 | 10E-3 |
| d301 | 42 | 58 | 10E-3 |
| KOS1.1 | 77 | 23 | 3-83 |
| n10 | 92 | 8 | 3-83 |
| n2 | 10 | 90 | 3-83 |

[a]The supernatant and pellet fractions were defined as the samples obtained by centrifugation after DNase 1 treatment (Knipe et al., 1986, J. Virol. 44:736).
[b]The antibody used for the Western blots to visualize ICP8 was rabbit polyclonal 3-83 (Knipe et al., 1987, J. Virol. 61:276) or mouse monoclonal 10E-3 (Rose et al., 1986, J. Gen. Virol. 67:1315). The negatives of the color reactions of Western blots were scanned by densitometer.

Viral DNA replication in mutant virus infected cells. To examine DNA replication in cells infected with each mutant virus under nonpermissive conditions, Vero cells were infected with each virus and [$^3$H]-thymidine was added to the cultures from 6 to 10 hours PI. The cells were harvested, and the DNA was isolated. Each DNA sample was digested with BamHI and XhoI and subjected to agarose gel electrophoresis. Each of the mutants was unable to replicate viral DNA as was the wild-type virus when grown in the presence of phosphonoacetic acid, a compound that preferentially inhibits the HSV-1 DNA polymerase.

The experimental details for the analysis of viral DNA now follow.

(i) Preparation of DNA. Plasmid DNA and viral DNAs were prepared as described by Knipe et al., *J. Virol.*, 29:698 (1979)). Viral DNA used for Southern blot analysis was purified as follows. Infected cells at a late times PI were frozen and thawed and then sonicated for 30 s at 0 to 4° C. Cell debris were removed by centrifugation at 480×g. The resulting supernatant was subjected to centrifugation at 23,500×g. Pellets were extracted with phenol-chloroformisoamyl alcohol (24:24:1) three times. After ethanol precipitation, the DNA was dissolved in a Tris-EDTA buffer.

(ii) Measurement of viral DNA synthesis. Cells were infected with the appropriate virus and labeled from 6 to 10 h with 20 µCi of [$^3$H]thymidine per ml, and total DNA was isolated by the method of Challberg (1986, Proc. Natl. Acad. Sci. USA 83:9094). The DNA was digested with the appropriate restriction enzymes and separated by agarose gel electrophoresis. After electrophoresis, the gel was treated with 1.0 M sodium salicylate for fluorography (Chamberlain, *Anal. Biochem.*, 98:132 (1979)).

DNA-binding properties of mutated ICP8. Prior to examining the DNA-binding properties of mutant ICP8 molecules, the solubility of the individual polypeptides was examined (Table 5) and was found to vary significantly. The DNA binding properties of the soluble mutated ICP8 molecules were then examined by chromatography through single stranded DNA-cellulose. Single stranded DNA cellulose chromatography of infected-cell extracts was performed as described (Knipe et al., *J. Virol.*, 44:736 (1981)), except that the cells were labeled from 4 to 6 hours PI with [$^{35}$S]methionine. Proteins were applied to columns containing single stranded DNA cellulose, and were eluted in increasing concentrations of NaCl. The majority of the ICP8 expressed in wild-type virus infected cells bound to the column, which was then eluted at an NaCl concentration of 0.5 M. In contrast, very little of the ICP8 expressed pm1 infected cells bound to the column. The amount of ICP8 which bound and was then eluted from the column was determined ad the results are presented in Table 5. ICP8 expressed in n10 infected cells bound to single stranded DNA-cellulose as efficiently and tightly as did wild-type ICP8. The lowest level of binding (21%) was observed for ICP8 expressed in d301 infected cells. ICP8 encoded by amino-terminal deletion mutants d101 and d102 bound to the DNA cellulose at levels of 72 and 75%, respectively. Based on these results it can be concluded that the portion of ICP8 from amino acid residues 564 to 1160 contains a region required for DNA binding.

TABLE 5

Ability of mutant ICP8 to bind to single stranded DNA cellulose
% of ICP8

| Virus | In flow through and wash | Eluted at indicated NaCl concn. | | | | Bound |
|---|---|---|---|---|---|---|
| | | 0.3 M | 0.5 M | 1.0 M | 4.0 M | |
| KOS1.1 | 2 | 23 | 67 | 8 | <1 | 98 |
| pm1 | 69 | 7 | 20 | 4 | <1 | 31 |
| n10 | 2 | 13 | 77 | 8 | <1 | 98 |
| d102 | 25 | 26 | 22 | 20 | 6 | 75 |
| d101[a] | 28 | 47 | 22 | 5 | <1 | 72 |
| d301[a] | 79 | 6 | 13 | 2 | <1 | 21 |
| n2[a] | 54 | 1 | 39 | 3 | <1 | 46 |

[a]Data obtained from densitometry of the negatives prepared from the Western blots.

Nuclear localization of ICP8 molecules encoded by viral mutants. Wild-type ICP8 localizes to the nucleus efficiently in infected cells (Fenwick et al., *J. Gen. Virol.*, 39:519 (1978); Knipe et al., *J. Virol.*, 43:314 (1982); Quinlan et al., *Mol. Cell. Biol.* 3:315 (1983); Quinlan et al., *Mol. Cell. Biol.*, 5:957 (1985)). The cellular distribution of wild-type and mutant ICP8 molecules was examined by indirect immunofluorescence which was performed according to Quinlan et al., *Mol. Cell. Biol.*, 3:315 (1983), using a 1:10 dilution of 793 anti-ICP8 monoclonal antibody and a 1:100 dilution of rhodamine-conjugated goat anti-mouse antibody for all mutant viruses except n2. A 1:30 dilution of anti-ICSP 11/12 polyclonal serum (Powell et al., *J. Virol.*, 39:894 (1981)) and a 1:200 dilution of fluorescein-conjugated goat anti-rabbit immunoglobulin were used for the detection of n2 ICP8. The n10 encoded ICP8 polypeptide, which lacks the last 36 amino acids from the carboxyl terminus and bound to a DNA as efficiently as wild-type ICP8, did not localize to the nucleus, rather it remained in the cytoplasm of infected cells. In contrast, the pm1 ICP8 polypeptide, which bound poorly to DNA, was found predominantly in the nucleus. These results clearly demonstrate that the nucleus localization signal(s) of ICP8 is separate from the DNA-binding function.

ICP8 encoded by d101 localized to the nucleus and was also capable of binding to DNA (Table 5), but this virus was incapable of viral DNA replication. The phenotype of this mutant provides genetic evidence that ICP8 has nuclear functions other than binding to DNA.

A summary of the phenotypic properties of the ICP8 mutants is presented below in Table 6.

TABLE 6

Phenotypic classes of ICP8 mutant viruses

| Group | Mutants | Growth on Vero cells | ssDNA binding[a] | Localization[b] |
|---|---|---|---|---|
| A | n10, d102 | − | + | C |
| B | pm1 d301 | − | − | N |
| C | n1 | − | + | C |
| D | d101 | − | − | N |

[a]+, >50% binding.
[b]Mutant ICPB molecules predominantly localized in the cytoplasm (C) or nucleus (N), as defined by indirecct immunofluorescence.

Replication Defective Mutants of HSV-1 Induce Cellular Immunity and Protect Against Lethal Infection Methods The following materials and methods were used in the examples described below.

Mice. Female Balb/c mice were purchased from Taconic Laboratory, Germantown, N.Y. and were used at 6 to 12 weeks of age. Mice were injected intraperitoneally with 0.5 ml of PBS or with 0.5 ml of virus suspended in PBS.

Viruses. The HSV-1 wild-type strain KOS 1.1 and strain mP were propagated and assayed on Vero cells as described (Quinlan et al., *Mol. Cell. Biol.*, 5:957 (1985)). A virus containing a mutation in the gene encoding ICP8, termed d301, was generated as described by Gao et al. supra. A virus containing a mutation in the ICP27 gene, termed n504R, was generated as described below. A virus (d120) encoding a mutated ICP4 gene was generated as described by DeLuca et al., *J. Virol.*, 56:558 (1985). VSV was propagated as described by Horn et al., *J. Virol.* 63:4157 (1989). All virus stocks were stored at −70° C. and a newly thawed aliquot from each stock was used in each experiment. Preparations of UV-irradiated HSV-1 and VSV were obtained by irradiating each virus at 0° C. using a 30-W UV source (G30T8; General Electric) for 45 minutes at a distance of 5 cm. Psoralen-inactivated virus preparations were generated by Lee Biomolecular (San Diego, Calif.).

Assays for T cell activity. Immune spleen cells were obtained from mice which had been inoculated intraperitoneally 3-4 weeks earlier with $10^6$ pfu of wild-type HSV-1, or with viral mutants containing mutations in the genes for either ICP4, ICP27 or ICP8. Mice which were inoculated with PBS served as negative controls. Spleen cells obtained from such mice were depleted of erythrocyte and polymorphonuclear leukocytes by Ficoll-hypaque gradient sedimentation. B lymphocytes were removed from the mixture by incubating splenocytes with antibodies specific for B lymphocytes for 30 minutes at 4° C. The cells were then washed and incubated with goat-rat-antibody coated latexpolymer beads containing a magnetic core (Advanced Magnetics, Cambridge, Mass.). J11-d2 positive cells which bound to the magnetic beads were then removed using a magnet (BioMag Separator, Advanced Magnetics). The remaining cells in the mixture consisting of >95% T cells, were washed and incubated at a concentration of $10^5$ cells/well in a total volume of 0.2 ml in 96 well round-bottom culture plates (Nunc, Roskilde, Denmark). Samples of cells were plated in quadruplicate. Responder cells were stimulated with UV-irradiated wild-type HSV-1. Control cells to which virus was not added were prepared in parallel. The cells were incubated in Dulbecco's modified Eagle medium (Hazelton), supplemented with 5% bovine calf serum (Hyclone Labs; which serum had been inactivated at 56° C. for 1 hour), 100 U/ml of penicillin (Gibco), 100 U/ml of streptomycin, 1 mM sodium pyruvate (Gibco), 0.1 mM nonessential amino acids (Gibco), 10-4 mM 2-mercaptoethanol (Sigma), and 2 mM-glutamine (Gibco). The cells were incubated for 3 days in the presence of 10% $CO_2$ at 37° C. [$^3$H]-thymidine (New England Nuclear), at a concentration of 1 µCi/well, was added for 6 hours and the cells were harvested using a Skratron Cell Harvester. The amount of radioactivity in each sample was determined using a liquid scintillation counter (Beta Trac 6895; TM Analytic).

Antibody assays. Samples of serum obtained from infected mice were analyzed for the presence of HSV-1 specific antibodies using an ELISA. The protocol used was similar to that described by Kahlon et al., *J. Inf. Dis.*, 158:925 (1988), adapted for murine serum. Microtiter plates (Linbro/Titertek) were treated with 0.1 ml of a 1:50 dilution of $10^7$ pfu HSV-1 suspended in PBS overnight. Serum obtained from mice immunized with each virus as described above was obtained by retroorbital bleeding of the mice. Microplates coated with HSV-1 were washed three times and incubated with 100 µl of a 1:100 dilution of serum followed by a 1:3 dilution of the same serum overnight at room temperature. The microplates were washed again and incubated with goat anti-mouse $IgG_2$ alkaline phosphatase at a 1:250 dilution (Southern Biotechnology) for 3 hours at 37° C. Thirty minutes after the addition of 1 mg/ml of the substrate for alkaline phosphatase (Sigma 104), the reaction was stopped by the addition of 75 µl of 3 N NaOH. The results of the experiment were obtained using an ELISA reader at 405 nm. Pooled serum from wild-type HSV-1 immunized mice served as a positive control and pooled naive mouse serum served as a negative control. Mouse sera were run individually, and the data are presented as mean and the standard errors of the mean.

Results

Use of replication defective viruses; lack of morbidity. To examine whether replication-defective viruses (i.e., those containing mutations in the genes encoding either ICP8 or ICP27) were lethal when inoculated into mice, mice were injected with either live wild-type HSV-1 or the mutant viruses d301 or n504. Mice which received as much as $10^8$ pfu of each mutant appeared healthy and were unaffected by the viruses. Littermates which received $10^7$ pfu of wild-type HSV-1 all died.

Induction of HSV-1 specific antibodies in mice inoculated with mutant viruses. To determine whether the mutant viruses were capable of inducing HSV-1 specific antibodies in mice, serum was obtained from the mice two weeks after inoculation (8 per group, intraperitoneal administration of $10^6$ pfu of d301, d504 and wild-type) and examined for the presence of HSV-1 specific antibodies (measured by ELISA). Reproducibly, while HSV-1 specific antibodies could be detected in the sera of these mice, the levels of the antibodies were markedly lower than those in the sera of mice inoculated with wild-type virus. A higher level of antibody was evident in sera obtained from mice inoculated with n504 than in the sera obtained from mice inoculated with d301. (FIG. 1) Similar results were obtained at both two and four weeks PI in a second independent experiment.

To determine whether expression of HSV-1 β proteins was necessary for induction of these antibodies, mice (8 per group) were inoculated intraperitoneally with $10^6$ pfu of the ICP4 deletion mutant d120 which does not express either β or γ proteins. While levels of antibodies specific for HSV-1 above control levels could be detected in the sera of these mice, these levels were significantly below those observed in sera from mice similarly inoculated with the ICP8 or ICP27 mutants (FIG. 1).

Figure 2:
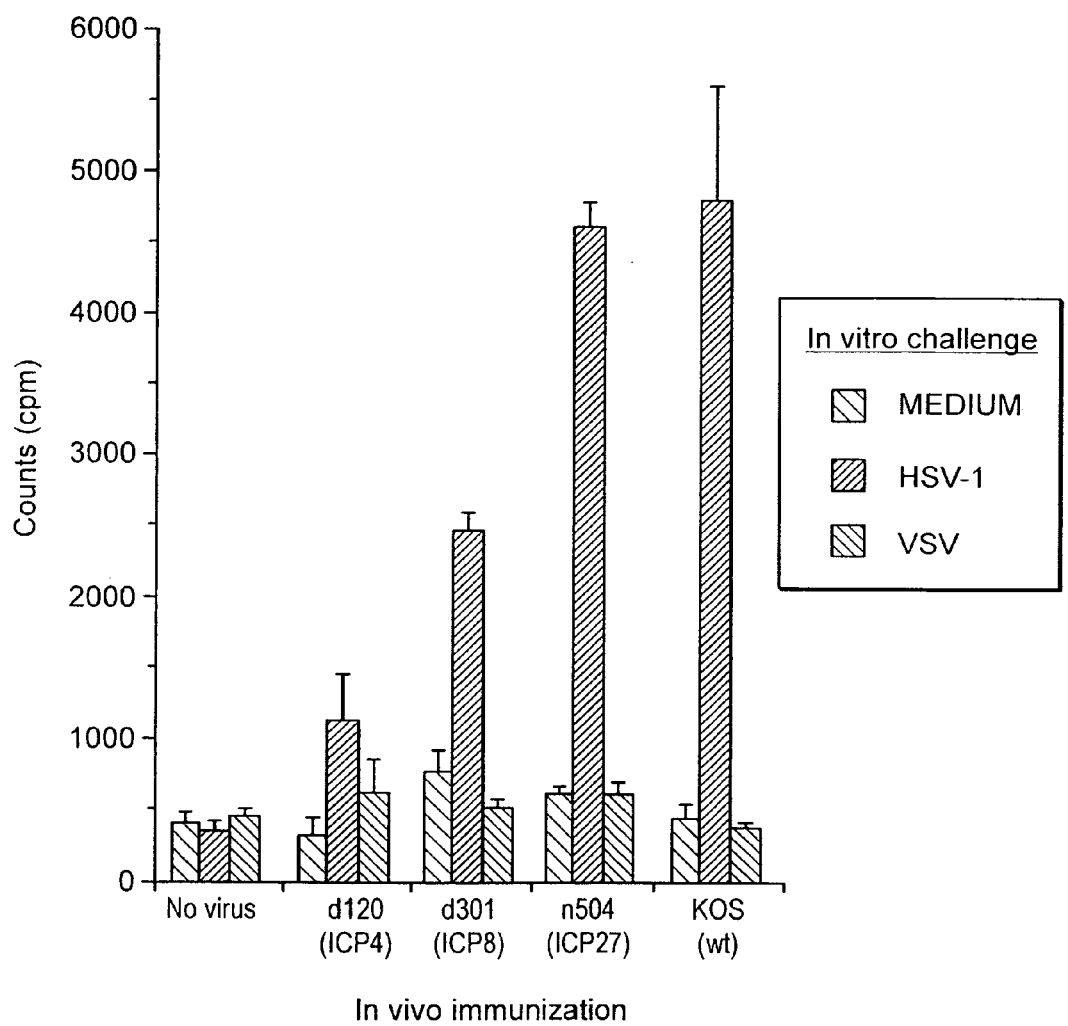
FIG. 2 is a graphical representation of the T cell response in mice inoculated with wild-type virus, and the replication defective mutants d120, d301 and n504.

Induction of T cell response in mice inoculated with viral mutants. To examine the ability of the mutants (each of which is deficient in the production of late viral gene products) to induce an HSV-1 specific T cell response, the response of splenic T cells obtained from inoculated mice viral antigens was measured in vitro. Mice received $10^6$ pfu of either live wild-type (KOS 1.1) virus or the replication defective mutants d120, d301 and n504. Three weeks later, T-cells obtained from mice in each group were incubated in vitro in the presence of UV-irradiated HSV strain mP (1 pfu/per cell). To control for the effect of non-specific T cell stimulation, the T cell response to an unrelated virus, VSV (1 pfu/per cell), was also evaluated. Splenic T cells from mice immunized with VSV not proliferate in response to HSV-1, while the same cells did proliferate in response to VSV. T cells obtained from non-immunized mice served as a negative control. Stimulation of T cell activity at levels above background was observed in splenic T cells obtained from mice inoculated with each of the replication defective viruses (FIG. 2). The results suggest that immunization of mice with the mutant viruses induced less stimulation of T cells than that induced followed immunization with wild-type virus. Notwithstanding, these mutant viruses induced substantial T cell reactivity (FIG. 2).

Figure 3:
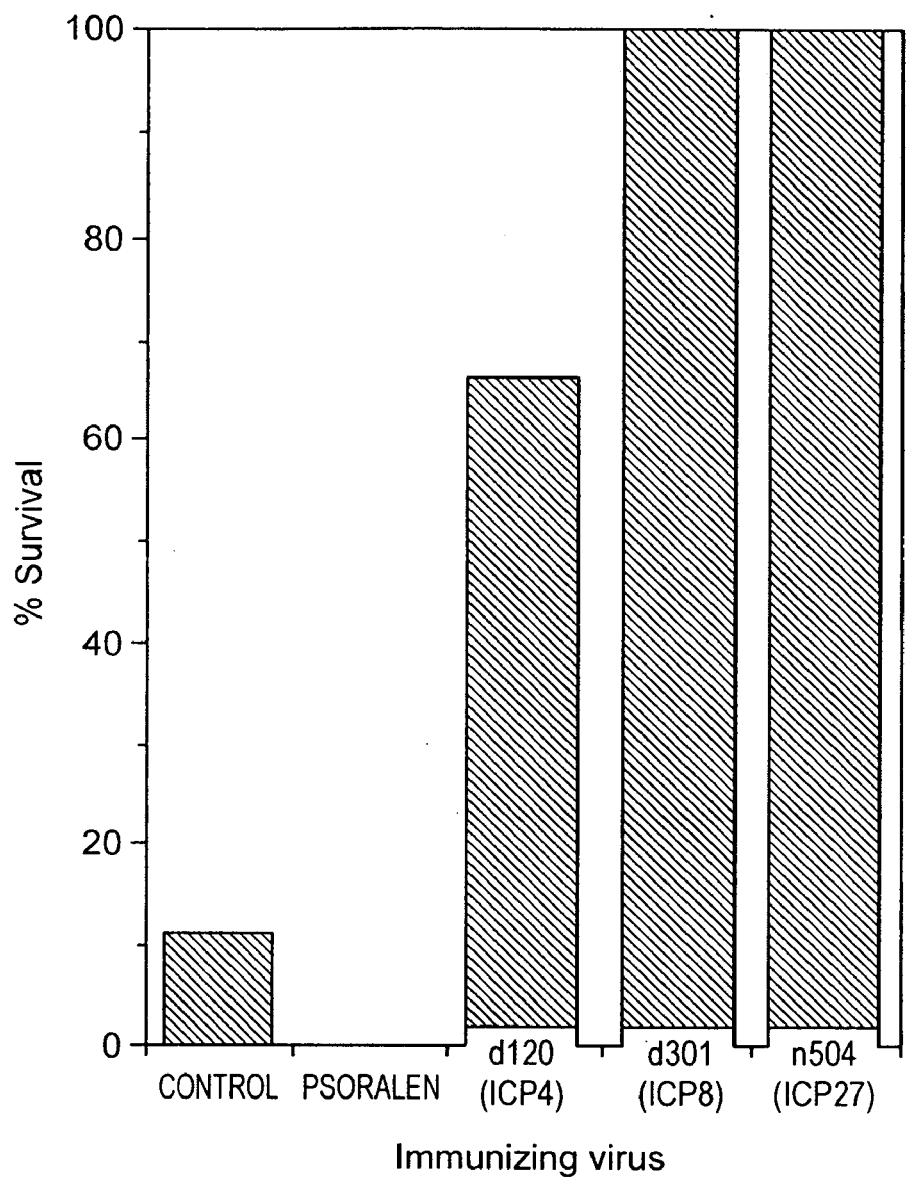
FIG. 3 is a graphical representation of the survival of mice inoculated with replication defective mutants that were subsequently challenged with wild-type virus.

Induction of protective immunity by replication-defective viruses. To assess the ability of replication-defective viruses to induce protective immunity to lethal HSV-1, groups of six mice were inoculated intraperitoneally with $10^6$ pfu of each of the replication defective mutants, d120, d301, n504 or an equivalent dose of psoralen-inactivated wild-type HSV-1 (5 mice). Control mice (9) were injected (i.p.) with PBS. Three to six weeks later (depending on the experiment), all the mice were challenged (i.p.) with a lethal dose ($5 \times 10^7$ pfu) of a virulent strain of HSV-1 (mP). In three separate experiments, mice which had been inoculated with the mutants d301 or n504 were protected against challenge by the wild-type virus, in that their survival rate was 100%. Control mice, which had received only the wild-type virus had a survival rate of less than 20%. Reproducibly, in subsequent experiments performed with all three mutant viruses (d120, d301 and n504), while only ⅑ control (PBS injected) mice survived, preinoculation of mice with either the ICP27 or ICP8 mutants resulted in 100% survival following challenge with wild-type virus. Even the ICP4 mutant (d120), which expresses only the immediate-early genes, protected the majority of mice. In contrast, UV irradiated virus had a minimal protective effect and immunization with psoralen-inactivated virus did not protect mice against lethal challenge (FIG. 3). Survival rates were recorded for 4 weeks, post-challenge. Most of the mice which died, died between day 7 and day 11, post-challenge.

In summary, replication-defective mutants of HSV-1 are capable of inducing both humoral and cellular immunity in mice inoculated with such viruses. Inoculation of mice with these mutants serves to protect these mice against challenge with a lethal dose of wild-type HSV-1. Since cellular immunity is especially important in protection against infection with herpes simplex virus (Whitley, 1990, In: *Virology*, ed. Fields and Knipe, Raven Press, p. 1843-1887), any agent capable of inducing such immunity is a potential vaccine candidate. Candidate vaccines such as those described above are also especially useful because they comprise viruses which are replication defective. Since these viruses cannot produce progeny viruses, they are substantially safer than conventional attenuated live virus vaccines. Mutant viruses such as those described above cannot replicate in cells which do not express a wild-type complementing form of the gene. They therefore cannot spread beyond the site of the initial infection. An important implication of this observation for the pathogenesis of herpesviruses is that such mutant viruses are unlikely to be capable of establishing a latent infection in the host into which they are introduced. Consistent with this theory is the fact that no evidence for a latent infection in mice inoculated on the cornea with either d301 or n504 could be detected when trigeminal ganglia obtained from these mice were examined by in situ hybridization for latency-associated transcription and expression. See generally, Coen et al. *Proc. Natl. Acad. Sci. USA*, 86:4736 et seq. (1989).

Replication Defective Mutants of HSV-1 Induce Immunomodulatory Effect

Materials

Balb/c By mice were purchased from the Jackson Laboratory, Bar Harbor, Me., and were used at 6 to 8 weeks of age.

Parental wild-type HSV-1 (KOS 1.1) and replication-defective mutants d301, n504 and d120 are described above. These mutants were grown and titrated on cells expressing the missing gene product, also as described above. These mutant viruses do not replicate in primate cells or mouse cells in culture. Inoculation of these mutant viruses onto mouse cornea does not lead to latent infection in the trigeminal ganglion, as evidenced by the absence of cells positive for hybridization with probes specific for the latency-associated transcript. In addition, infection of mice after corneal scarification results in minimal levels of viral DNA in the trigeminal ganglion. Thus, there is no evidence of spread of these mutant viruses in infected mice. Because there is no evidence that any normal host cell function can complement these defects in ICP8 or ICP27, it is reasonable to conclude that these mutants are replication-defective in mice as well as in cultured cells. Wild-type HSV was titrated using Vero cells. Psoralen-inactivated virus was obtained from Lee Biomolecular Research Laboratory (San Diego, Calif.) and had no detectable titer in plaque assay. UV-irradiated HSV was prepared by irradiating the virus at 0° C. by using a 30-W UV source (G30t8; General Electric) for 1 hour at a distance of 5 cm. UV irradiation resulted in a 5 to 6 log decrease in viral titer. Purified hamster anti-TNF antibody was the kind gift of Dr. Robert Schreiber (Washington University, St. Louis, Mo.).

In vivo Antibody Treatment

Monoclonal rat anti-mouse IFN-γ (F3) (Amgen, Boston, Mass.) or an irrelevant purified rat IgG (Amgen) was injected i.p. into mice on days −1, 0, and 1. On day 0 mice were also challenged with $10^6$ pfu of HSV-1 (mP strain).

Total Isotype Assays

Total subclass IgG1 and IgG2a concentrations were determined by a standard ELISA. Briefly, goat anti-mouse Ig (Tago) was incubated at a concentration of 2.5 µg/ml in PBS using 96 U-bottomed microtiter plates (Linbro/Titerteck). This was either incubated at room temperature overnight or at 37° C. for 2 hours. The plates were then washed with PBS and 0.1% Tween 20. Appropriate dilutions of serum were assayed in duplicate. Monoclonal mouse IgG1 and IgG2a were used as standards for calculation of subclass-specific levels. After washing three times, 100 µl of appropriately diluted alkaline phosphatase-conjugated goat anti-mouse IgG1 and IgG2a (Southern Biotechnology, Birmingham, Ala.) were added, incubated at 37° C. for 3 hours and washed. Wells were developed with 100 µl of DEA buffer for 30 minutes at room temperature. The reaction was stopped by adding 75 µl of 3 M MaOH and the OD was read in an ELISA reader.

HSV-specific IgG1 and IgG2a Assays

The ELISA assay for HSV-specific antibodies was adapted for use with mouse serum from that described by Kahlon et al., supra. The calculation of the HSV-specific antibodies was performed by the method of Zollinger et al., *J. Immunol. Methods*, 46:129 (1981). This method has been utilized by others to quantitate Ag-specific antibodies to a variety of Ag, including tetanus as well as bacterial proteins and polysaccharides. Briefly, an IgG2a-HSV-specific assay was run in parallel with a total mouse IgG2a assay. One microtiter plate was coated with cell-free HSV-1 produced from infected Vero cells. Virus was diluted in PBS at a concentration of $2 \times 10^5$ pfu/ml at room temperature overnight. Plates were then washed three times using PBS-Tween. A series of dilutions of a pooled serum from mice infected with HSV were incubated with HSV-coated plates at room temperature overnight. This pooled mouse serum was used as a reference standard for all assays in the subsequent experiments. To convert absorbance units to micrograms of antibody the following procedure was utilized: half of the wells of a 96-well plate were coated with anti-mouse IgG2a antibody and the other half with HSV. Serial dilutions of a known concentration of an IgG2a mAb (Tago) were added to the wells coated with anti-mouse IgG2a and dilutions of the pooled anti-HSV serum were added to the wells with HSV. The following day (after washing three times with PBS and Tween) 100 µl of appropriately diluted alkaline phosphatase goat anti-mouse IgG2a (Southern Biotechnology) were added to each well and the plate was again incubated at 37° C. for 3 hours. After the last rinse, wells were developed with 100 µl of DEA buffer. The reaction was stopped by adding 75 µl of 3 N NaOH, and absorbance was read at 405 nm using an automated ELISA reader. By plotting the OD obtained from the interaction of the goat anti-mouse IgG2a and known concentrations of IgG2a vs the OD of the HSV-specific assay, we converted the units of anti-HSV IgG2a in our pooled serum to micrograms of HSV-specific IgG2a. An OD was read at a suitable point on the IgG2a standard curve and on the HSV Ag-antibody curve, and units were calculated as described in Zollinger et al, supra, and Pasatiempo et al., *FASEB J.*, 4:2518 (1990). The same method was utilized to measure HSV-specific IgG1. In all assays, samples and standards were run in duplicate. This assay was tested for its specificity by simultaneously screening plates coated with media or VSV, as an irrelevant control virus.

Results

Figure 6:
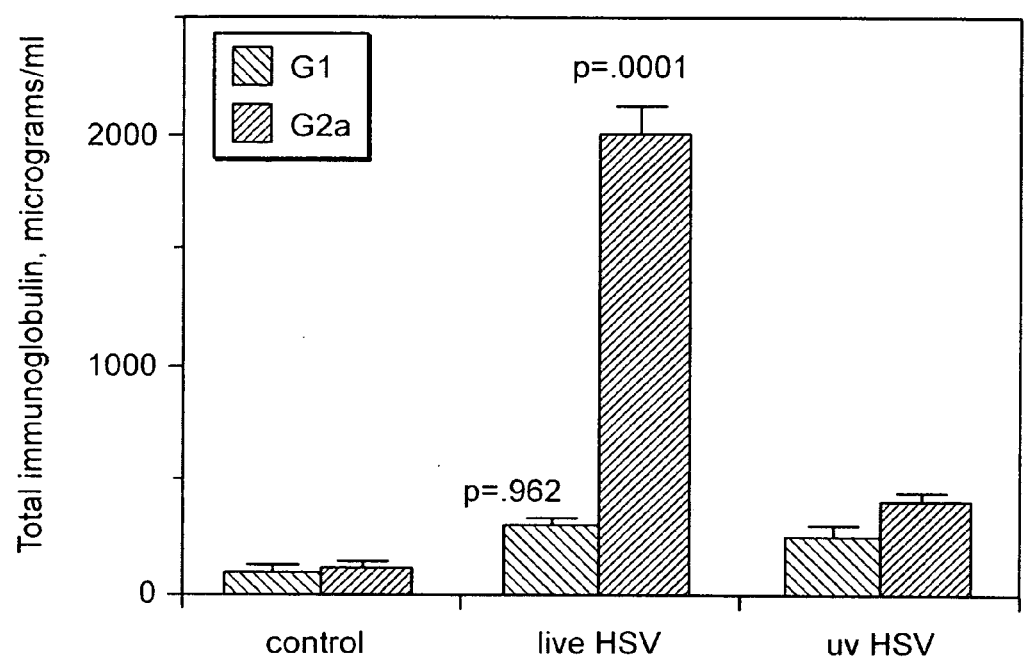
FIG. 6 is a graphic illustration of the total IgG2a and IgG1 antibody production after immunization of mice with live, UV-inactivated HSV (mP strain) or PBS (control).

Virus-induced Subclass Shift is not Observed after Challenge with Inactivated Virus To examine the subclass distribution of murine Ig subclass IgG2a and IgG1 after immunization, Balb/c mice (4 per group) were challenged with $10^6$ pfu of live or UV-inactivated HSV (mP strain) or a medium control. The mP strain of HSV-1 was utilized because it is a pathogenic strain in Balb/c mice. Two weeks after i.p. infection, sera were obtained through retroorbital bleeding. Serum levels of total IgG2a, IgG1, HSV-specific IgG2a, and HSV-specific IgG1 were measured by ELISA. A 15- to 20-fold increase of total IgG2a subclass antibody was observed in the mouse group injected with live virus, whereas this marked increase was not observed in mice challenged with UV-inactivated virus (FIG. 6, representative of our experiments). The increase in the total IgG1 level was not significant (p=0.962 by Student's t-test). Similar results were obtained at weeks 3 and 4 post-infection.

Figure 7:
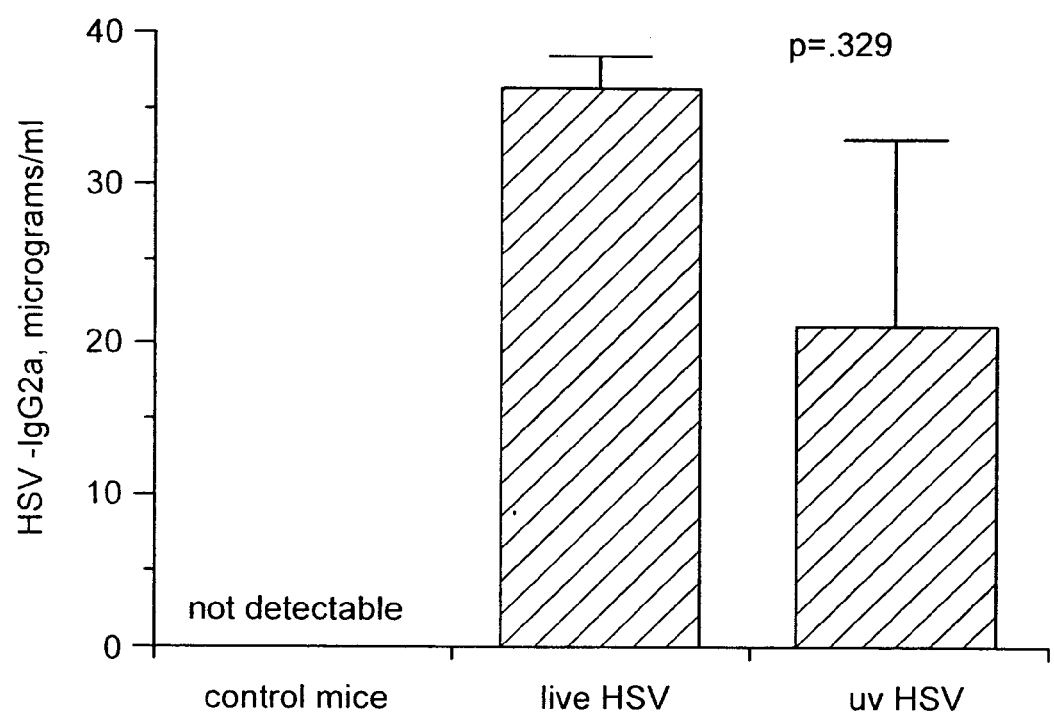
FIG. 7 is a graphic illustration of the production of HSV-specific IgG2a in sera from the mice described in FIG. 6.
Figure 8:
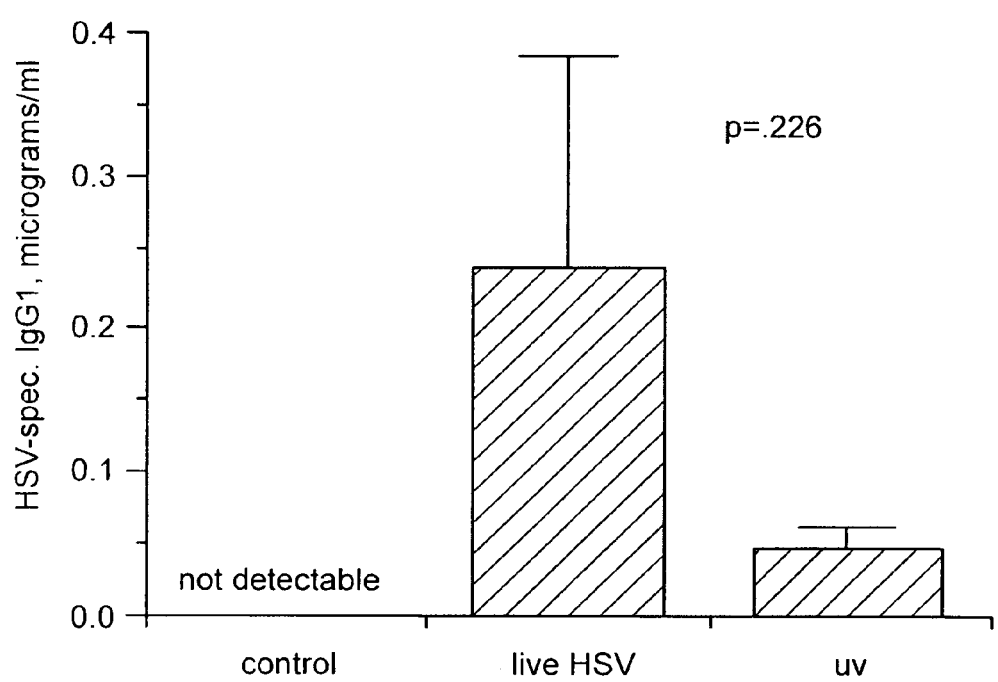
FIG. 8 is a graphic illustration of the production of HSV-specific IgG1 in sera from the mice described in FIG. 6.

While the total increase in IgG2a resulting from challenge with live virus was more than 1 mg/ml, the amounts of IgG2a which bound to HSV-coated plates were less than 100 µg in several assays performed (FIGS. 6 and 7A). This increase in total Ig induced by live viral infection was predominantly a nonspecific poly-clonal effect. Both live as well as inactivated virus were capable of inducing virus-specific antibody (FIGS. 7 and 8), while only the live virus induced a dramatic subclass shift (FIG. 6). The differences in the levels of HSV-specific IgG2a and HSV-specific IgG1 from mice challenged with live versus UV-inactivated virus is not statistically significant (students t-test). These data suggested that the processes leading to the induction of the subclass shift were distinct from those which lead to production of virus-specific antibody.

Figure 9:
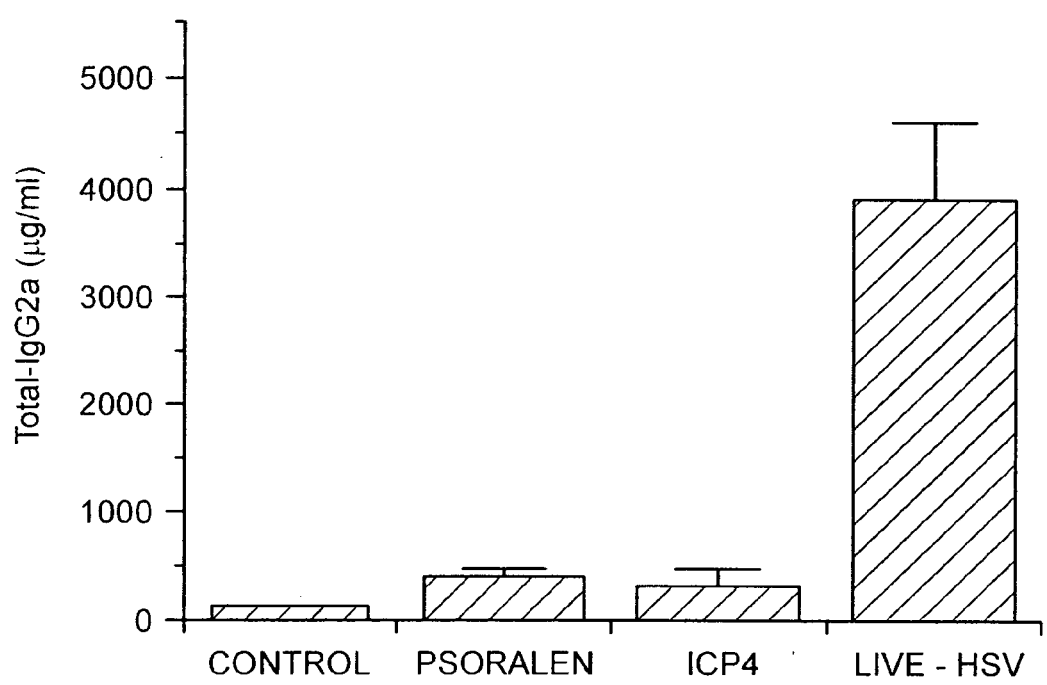
FIG. 9 is a graphic illustration of the production of IgG2a after immunization of mice with live, psoralen-inactivated, or d120 (ICP4-) HSV, or PBS (control).

Psoralen-inactivated Virus and Immediate-early Infected Cell Protein 4 (ICP4) Deletion Mutant Subclass Virus Failed to Induce Shift Live viruses are usually capable of replicating in the host and therefore may invade tissues which are not accessible to inactivated viruses or killed proteins. In this experiment replication-defective mutant strains of HSV which could not spread in the host were employed. Because UV inactivation may not lead to loss of all infectivity and there was a possibility of some live virus, psoralen-inactivated virus was tested on the isotype profile. Mice (8 mice per group) were challenged with $10^6$ pfu with live virus, psoralen-inactivated virus, or HSV-1 strain d120. Whereas immunization of mice with live virus induced a pattern of Ig distribution characterized by an IgG2a predominance, a significant isotype switch was not observed in mice challenged with psoralen-inactivated virus or the replication-defective d120 mutant virus (FIG. 9).

Figure 10:
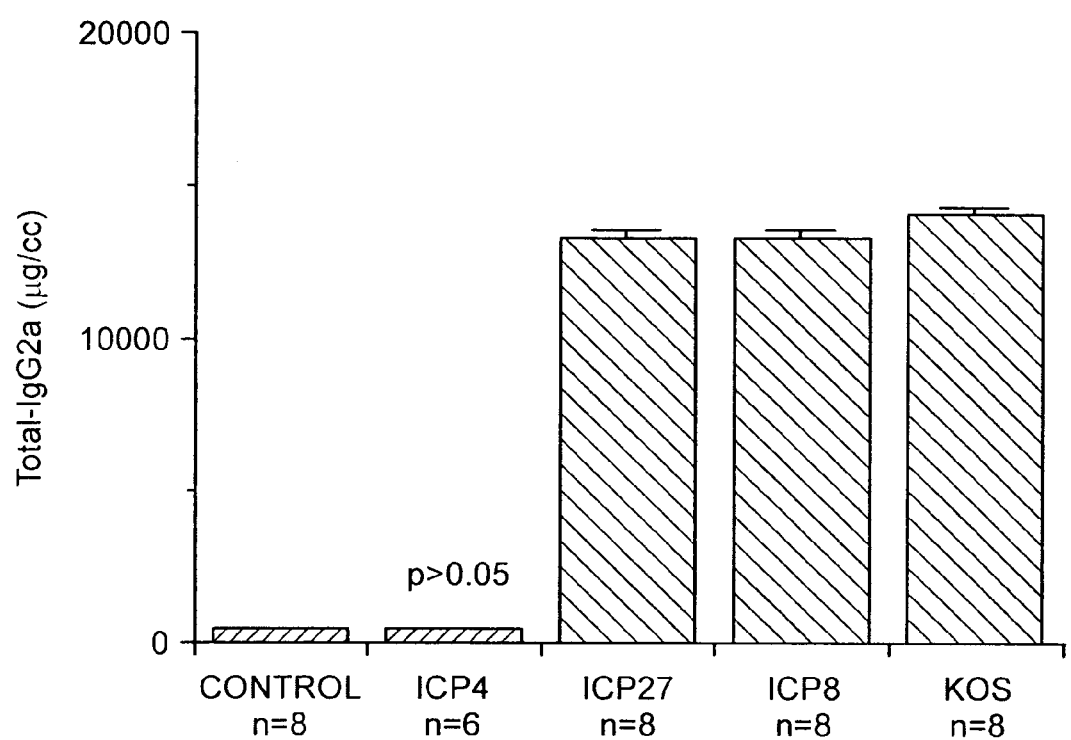
FIG. 10 is a graphic illustration of the production of IgG2a after immunization of mice with live (KOS), d120 (ICP4-), d301 (ICP8-), n504 (ICP27-) or PBS (control).

Two Replication-defective Mutant Viruses with Late Replication Blocks Induced the Subclass Shift To define better which aspects of the viral replication process might be inducing the effect noted, we used viruses blocked at two other points in the virus life cycle. Mice were bled 2 weeks after challenge with either $10^6$ pfu of ICP4-(d120), ICP27-(n504), ICP8-(d301) mutant or parental HSV-1 (KOS 1.1 strain) viruses. Control mice were injected with PBS. Total immunoglobulin IgG2a levels were measured by ELIAS. Data were presented as the mean and standard error of the mean. This experiment is representative of 3 performed. While the ICP4 deletion mutant failed to induce the subclass switch, another HSV-1 mutant (n504) with a nonsense mutation in the gene encoding ICP27 was able to induce a subclass shift similar to wild-type virus. This was despite the fact that, like the ICP4 mutant virus, it could not replicate. The same effect was also produced by another replication-defective mutant that fails to encode a functional early protein, ICP8 or the major DNA-binding protein, mutant d301 (FIG. 10). Thus, specific components of the viral replication cycle, and not production of infectious progeny virus, are required for induction of the subclass shift.

Purified mAb to Mouse IFN-γ can Affect Subclass Switching

Figure 11:
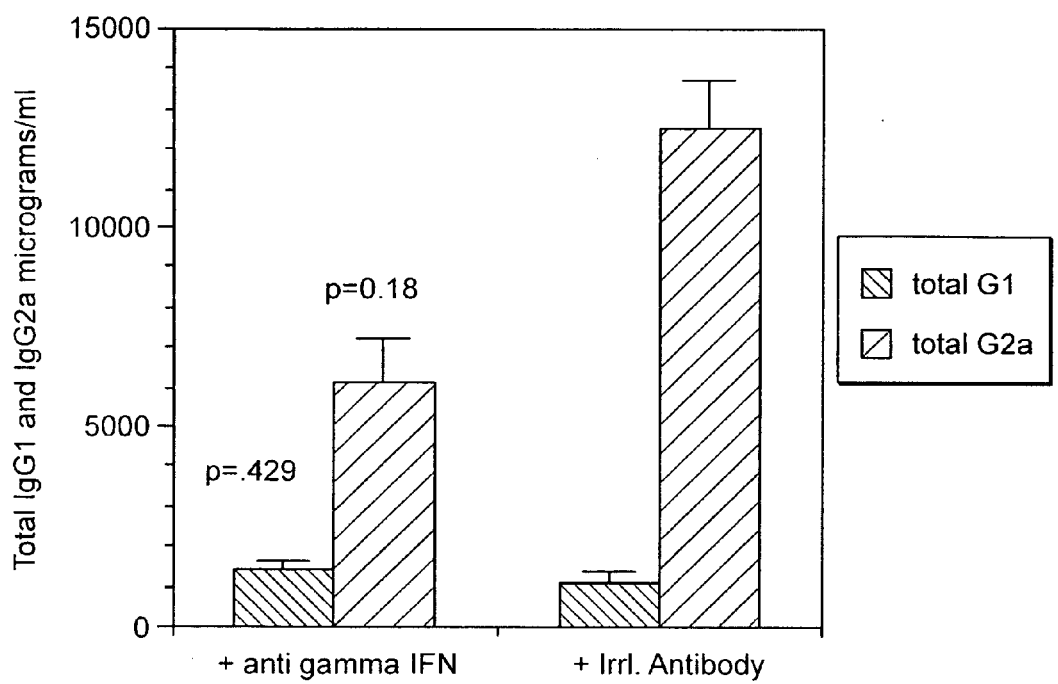
FIG. 11 is a graphic illustration of the effect of anti-IFN-γ antibody on the subclass shift in mice challenged with live HSV-1.

To assess the role of the cytokine IFN-γ in producing the subclass switch during viral infection, we injected mice with purified mAb to mouse IFN-γ to examine its effect on IgG2a production in vivo. Balb/c mice (4 per group) were injected with either 2 mg of purified mAb to mouse IFN-γ or 2 mg of an irrelevant isotype matched control on days −1, 0, and +1 i.p. On day 0, mice were also challenged with $10^6$ pfu of live HSV-1 (mP strain). Injection of the mAb to IFN-γ, beginning 1 day before challenge followed by two subsequent doses, partially blocked the virus-induced IgG2a production (FIG. 11). One week later, mice were bled retro-orbitally and total IgG2a and IgG1 were measured individually per ELIAS. There was no effect of the anti-IFN-γ antibody on the total IgG1 level, indicating that this was not a nonspecific effect. The antibody administration had no effect on HSV-specific IgG2a, suggesting that the IFN-γ antibody eliminated the polyclonal effect but not the Ag-specific response. FIG. 11 is representative of three performed.

Immunization and IgG2A/IgG1 Subclass Shift with the ICP8-Deleted HSV-β-Galactosidase Mutant Immunization of Balb/c Mice Female Balb/c mice were immunized with the ICP8-deleted HSV-β-galactosidase mutant (HSV-β-gal). Primary immunization was with $10^6$ pfu in 0.1 ml ip. Mice were bled for serum 11 days later and boosted with $10^6$ pfu in 0.1 ml sc. Serum was again obtained 28 days post-booster immunization.

Mice were also immunized with β-galactosidase (Grade VIII: from E. coli, Sigma Chemical Co). Primary immunization of 100 µg protein in Incomplete Freund's Adjuvant (0.2 ml sc) was followed 14 days later with a boost of 100 µg soluble protein (0.1 ml sc). Serum was obtained 11 days post booster immunization for antibody determination.

Determination of Antibody to β-galactosidase by ELISA

Immunlon® 2 microtiter plates (Dynatech Laboratories) were coated with 1 µg/ml of β-galactosidase (Sigma) in phosphate-buffered saline (PBS) at 37° C. for 90 minutes. Plates were washed three times with PBS Tween (PBS+ 0.5% Tween 20, Sigma). Serum samples were diluted in PBSTween and incubated on the plate for 2 hours at room temperature. Plates were washed again and affinity purified alkaline phosphatase conjugated goat antibodies to mouse IgG subclasses (Southern Biotechnology Associates) diluted in PBS. Tween was added and incubated for 2 hours at room temperature. All detecting antibodies were assayed to insure subclass specificity. Plates were washed and developed at room temperature with Sigma 104® phosphatase substrate at 1 mg/ml in diethanolamine buffer. IgG1 and IgG2a assays were allowed to develop for 30 minutes, IgG2b and IgG3 assays for 60 minutes, then read at OD 405 nm on a Vmax® Microplate Reader (Molecular Devices).

ELISA results are reported as the reciprocal dilution of serum producing an OD of 0.75 after 30 minutes for IgG1 and IgG2a assays. Results for IgG2b and IgG3 assays are reported as the reciprocal dilution producing an OD of 0.5 after 60 minutes.

TABLE 7

| Antigen | IgG1* | IgG2a* | IgG2b** | IgG3** | IgG2a/IgG1 Ratio |
|---|---|---|---|---|---|
| HSV-β- | 300 | 1,200 | <20 | 60 | 4.0 |
| gal, 2° | 550 | 320 | <20 | 70 | 0.58 |
|  | 350 | 1,000 | <20 | 50 | 0.29 |
|  | 400 | 130 | <20 | 50 | 0.33 |
| MEAN | 400 | 710 | <20 | 58 | 1.3 |
| β-gal, | 60,000 | 900 | 2,000 | 2,000 | 0.015 |
| 2° | 36,000 | 270 | 150 | 1,700 | 0.008 |
|  | 18,000 | 750 | 300 | 3,000 | 0.042 |
|  | 48,000 | 1,200 | 800 | 1,300 | 0.025 |
|  | 8,000 | <20 | <20 | 350 | <0.003 |
|  | 17,000 | 900 | 400 | 1,300 | 0.053 |
| MEAN | 31,167 | 672 | 610 | 1,608 | 0.029 |

*reciprocal titer giving OD 0.75
**reciprocal titer giving OD 0.50

This evidence demonstrates that a humoral response is elicited by a foreign antigen expressed by a replication-defective HSV strain, providing evidence for the feasibility of this proposed research. In addition, the antibody isotype was different from that elicited by injection of β-galactosidase protein which produced an IgG2a:IgG1 ratio of 0.003-0.053. High IgG1 levels are associated with Th2-mediated responses to protein antigens, and high IgG2a antibodies are associated with Th1-mediated responses to live virus antigens. These results suggest that the Th1 mediated response is also conferred onto the vector-expressed heterologous antigen.

Construction, Characterization, and Prophylactic Immunization Against Genital Herpes with an HSV-2 Virus Containing Mutation in the ICP8 Gene Isolation of pICP8-lacZ from HSV-1 HD-2 strain. HSV-1 HD2 (lac2 insertion in ICP8 gene) viral DNA was digested to completion with BamHI and electrophoresed on a 0.7% low-melt agarose gel. The ICP8-lacZ fusion gene was expected to be contained within the largest fragment obtained (approx. 12.6 kbp) unique to HD2. Restriction analysis comparison with the HD2 parental virus, KOS 1.1, revealed this to be so. This band was excised from the gel and cloned into the BamHI site of plasmid pNEB193 (New England Biolabs). Following transformation, white colonies on LB plates containing the chromogenic substrate for β-galactosidase, X-gal, were selected and screened for the correct insert. The identity was confirmed by restriction digestion analysis.

Isolation of HSV-2 recombinants. For marker transfer of the ICP8-lacZ fusion sequences into HSV-2, pICP8-lacZ was digested with KpnI, and the largest fragment (approx. 6.4 kbp) was purified following agarose gel electrophoresis. The 5' end of this fragment was 76 codons downstream of the initiation codon and the 3' end was approximately 1.3 kbp upstream of the gB promoter. The purified fragment was cotransfected at several molar ratios with 1 µg of HSV-2 strain 186 syn+-1 wt-viral DNA into S-2 (which express ICP8 upon viral infection) cells using the calcium phosphate method. Following the appearance of plaques, the infected cells were harvested by the addition of half volume of sterile milk freeze-thawed twice, sonicated and dilutions plated on S-2 monolayers in 6-well plates. Infected monolayers were overlaid with 199 medium −1% calfserum (199V) containing 0.1% immune serum and incubated at 37° C.

Screening for recombinants. Plaque formation was usually observed within two days of plating on the S-2 monolayers. Cell monolayers were then washed twice with 199V medium and overlaid with 199V medium containing 0.5% agarose and 300 µg/ml of X-gal, chromogenic substrate for β-galactosidase, producing a blue color when metabolized by the enzyme. Recombinant viruses containing the ICP8-lacZ insert were expected to produce blue plaques in the presence of X-gal. Blue plaques were picked and dilutions plated on both S-2 and Vero monolayers. Those isolates that formed blue plaques on S-2 monolayers but not on Vero monolayers were considered for further purification on S-2 cells. Once purified, the isolates were tested for growth on Vero cells and none was observed except for a generalized cytopathic effect (CPE) observed at low viral dilutions. Viral recombinants were obtained at a frequency of around 0.1%. Two independently isolated mutants, 5BlacZ and 20BlacZ, were characterized further.

Analysis of HSV-2 Recombinant Virus

1. Replication in Different Cell Lines. Replication of the 5BlacZ mutant virus was assayed on different cell lines by plaque formation. 5BlacZ formed plaques efficiently on S-2 cells which express ICP8 upon HSV infection (Table 8) but did not show detectable plaque formation on Vero cells (Table 8). In contrast, the wt parental virus, HSV-2 strain 186, formed plaques equally well on both cell lines.

2. Genomic analysis. The viral mutants were analyzed initially by restriction digestion and Southern hybridization analysis. Viral DNA was purified by sodium iodide gradient centrification and subjected to restriction analysis with several enzymes. The probe used in the Southern blots was linearized pICP8-lacZ labeled with $^{32}$P-dCTP by the random primer method. This analysis confirmed the presence of the ICP8-lacZ gene at the expected location of the two recombinant HSV-2 viruses (FIG. 2). Further analysis was performed using only 5BlacZ.

TABLE 8

| | Viral Titer (PFU/ml) | |
|---|---|---|
| Virus | Vera Cells | S-2 Cells |
| 5BlacZ | <10$^{3a}$ | 4.5 × 10$^8$ |
| 186 syn+-1b | 1.8 × 10$^8$ | 1.3 × 10$^8$ |

$^a$No plaques were observed at a 1:1000 dilution of the virus stock. At lower dilutions generalized CPE was observed.
$^b$Wild-type parental strain from which 5BlacZ was derived 3. Gene expression. To compare gene expression by 5BlacZ and wt virus, Vero cells were infected with 5BlacZ or HSV-2 186 syn$^+$-1 virus at a multiplicity of infection (MOI)=20. At various times postinfection, the cultures were labeled with $^{35}$S-methionine. Cell lysates were prepared and subjected to electrophoresis in 9.25% SDS gels. The 5BlacZ virus expressed the same proteins as wt virus, except that somewhat reduced amounts of late proteins, such as ICP5 and ICP25, were expressed by the mutant virus as compared with the wild type virus. In Western blot analyses of these extracts, expression of the viral glycoproteins gB and gD in mutant-infected cells was approximately one half that in wt virus-infected cells. Thus, the 5BlacZ mutant virus expressed viral proteins of all kinetic classes in normal cells, which would be expected to induce an immune response in an inoculated host.

4. DNA replication. To examine the ability of 5BlacZ to replicate its DNA, Vero cells were infected with either wild-type strain 186 syn$^+$-1 or the ICP8 mutant, 5BlacZ at an MOI of 20 or mock infected. Following infection, cells were overlaid with 199V medium for 3 hours and then the medium was replaced with 199V containing 25 μCi/ml of $^3$H-thymidine and incubation continued for 4 more hours. Following cellular lysis and RNase A treatment, total DNA was recovered. Equal amounts of DNA were then digested with both EcoRI and XbaI and subjected to agarose electrophoresis. The gel was then fluorographed in Entensify™ (New England Nuclear), dried and exposed to Kodak XAR film at −80° C. for 3 days. The autoradiogram revealed that 5BlacZ was unable to replicate its DNA.

5. Cell Killing. The ability of 5BlacZ to kill infected Vero cells was determined by infecting confluent monolayers in T25 flasks at an MOI of 5 and harvesting at 24, 48 and 72 hours post-infection. Cells were resuspended in a 0.5% (w/v) solution of trypan blue in phosphate-buffered saline and counted in a hemocytometer. Total cell counts were determined; dead cells were distinguished from live ones by their uptake of trypan blue dye (FIG. 12). Thus, although 5BlacZ is replication-defective, it kills infected cells and does not persist, a desired property in a vaccine virus.

6. Immunization with the HSV-2 5BlacZ replication-defective mutant against Genital Herpes Infection in Guinea Pigs.

Experimental Design: Thirty six female Hartley guinea pigs (Charles River Breeding Laboratories, Wilmington, Mass.) were randomized into three groups. Group 1 (N=12) were unimmunized controls. Group 2 (N=12) received 0.5 ml of a suspension containing 1×10$^7$ PFU of 5BlacZ virus by subcutaneous injection on the back. Group 3 (N=12) received 0.5 ml of a suspension containing 1×10$^7$ PFU of 5BlacZ by injection into the two rear footpads. Viral challenge was performed on day 33 post immunization. The animals were inoculated with challenge virus by rupturing the vaginal closure membrane with a moistened calcium alginate tipped swab (Calgiswab #3, Spectrum Labs, Los Angeles, Calif.) and instilling 0.1 ml of a virus suspension containing 5.7 log$_{10}$ PFU of HSV-2 strain MS into the vaginal vault using a plastic catheter (Abbocath, Abbot Labs, North Chicago, Ill.). To maximize the number of animals infected, the inoculation procedure was repeated 30 minutes later. Vaginal swab samples were collected on days 1, 2, 3, 5, 7, and 10 post-inoculation (PI) and stored frozen (−70° C.) until assayed for the presence of virus by titration on primary rabbit kidney cells. Guinea pigs were evaluated daily and the severity of primary genital skin disease quantified using a lesion score-scale described previously (Stanberry L R, E R Kern, T M Abbot, and J C Overall. 1982. Genital herpes in guinea pigs: pathogenesis of the primary infection and description of recurrent disease. J. Inf. Dis. 146:399-404). Primary genital skin disease was defined as any primary episode of clinical disease beginning before day 10 PI. Following recovery from primary infection, animals were examined daily from days 15-42 PI for evidence of spontaneous recurrent herpetic disease.

TABLE 9

Effect of Immunization on Primary and Recurrent Genital Skin Disease

| Group | Primary Genital Disease | | Recurrent Genital Disease |
|---|---|---|---|
| | Number[a] | Severity[b] | Number[c] |
| 1 (Unimmunized) | 11/12 | 8.41 ± 0.48 | 6/7 |
| 2 (Subcutaneous) | 6/12[d] | 4.50 ± 0.52[f] | 7/12 |
| 3 (Footpad) | 3/11[e] | 1.00 ± 0.29[fg] | 5/11 |

[a]Number of Animals with clinical disease/number of animals in which virus could be isolated from genital tract.
[b]Mean + SE. Severity measured as area under the lesion score-scale curve. Calculated using only symptomatic animals.
[c]Number of animals with recurrent disease/number of infected animals which could be assessed for recurrences from days 15–42 PI
[d]$p < 0.07$ compared to untreated controls (Fisher's 2-tail exact test)
[e]$P < 0.003$ compared to untreated controls (")
[f]$P < p.001$ compared to untreated controls (")
[g]$P < 0.05$ compared to subcutaneous immunized animals (Bonferroni correction of ANOVA)

TABLE 10

Effect of Immunization of Challenge Virus Replication in the Genital Tract

| | Mean Viral Titer in the Genital Tract (log$_{10}$/ml) on Day | | | | | |
|---|---|---|---|---|---|---|
| Group | 1 | 2 | 3 | 5 | 7 | 10 |
| 1 (Un-treated) | 5.55 | 5.79 | 4.35 | 3.09 | 3.3 | 0.44 |
| 2 (Subcutaneous) | 5.99 | 4.58 | 3.24 | 1.02 | 0.18 | 0 |
| 3 Footpad | 4.9 | 4.66 | 3.85 | 1.42 | 0.53 | 0.13 |

These results show that immunization of guinea pigs, especially by footpad inoculation, leads to protective immunity that reduces genital lesions and HSV-2 replication in the genital tract when the animals are inoculated intravaginally with a virulent wild type strain of HSV-2. These results provide evidence that a replication-defective mutant strain of HSV-2 can provide prophylactic immunity against genital herpes.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of eliciting an immune response treating herpetic stromal keratitis in a mammal, the method comprising administering to the mammal an effective amount of a mutated herpesvirus in a pharmaceutically acceptable carrier, the herpesvirus having a mutation in one or more genes encoding a protein essential for viral genome replication to render the herpesvirus replication defective, said mutant herpesvirus having an ability to effect an antibody subclass shift of IgG2a/IgG upon in vivo administration to said mammal.

2. The method of claim 1 wherein the herpesvirus is selected from the group consisting of HSV-1, HSV-2, VZV, EBV, CMV, HHV-6 or HHV-7.

3. The method of claim 2 wherein the herpesvirus is HSV-1 or HSV-2.

4. The method of claim 3 wherein the mutation is in the gene or genes encoding the proteins ICP8 or ICP 27.

5. A composition in a pharmaceutically accepted carrier comprising:
a mutated herpesvirus characterized by a mutation in at least one gene encoding a protein essential for viral genome replication of said herpesvirus, thereby, rendering the virus genome replication defective; and, the herpesvirus comprising one or more heterologous genes; wherein, the mutated herpesvirus is capable of infecting a mammalian cell and of eliciting an immune response to heterologous gene products in a mammal treated with the herpesvirus.

6. A composition comprising a mutated herpesvirus capable of infecting a mammalian cell; said herpesvirus comprising a mutation in one or more early genes encoding a protein essential for viral genome replication to render the herpesvirus replication defective; and, said herpesvirus comprising one or more heterologous genes encoding heterologous gene products; wherein, the mutated herpesvirus is capable of infecting a mammalian cell and of eliciting an immune response to heterologous gene products in a mammal treated with said herpesvirus.

7. A method of inducing an immune response in a mammal against immunogen, the method comprising administering to said mammal an immune response inducing effective amount of an immunogenic composition comprising a mutated herpesvirus in a pharmaceutically accepted carrier, said herpesvirus having a mutation in one or more genes encoding a protein essential for viral genome replication to render the herpesvirus replication defective, said herpesvirus further comprising one or more heterologous genes encoding said immunogen.

8. An immunogenic composition comprising a pharmaceutically acceptable carrier and a mutated herpesvirus capable of infecting a mammalian cell and of eliciting an immune response in a mammal immunized with the composition, wherein the herpesvirus includes two or more mutations, at least one of the mutations being in the genes encoding HSV-1, ICP27; or HSV-1, ICP8; or in a corresponding early gene in a non-HSV-1 herpesvirus, and the mutation renders the herpesvirus incapable of replication, wherein one mutation is a deletion mutation and the other mutation is a nonsense mutation.

9. An immunogenic composition comprising a pharmaceutically acceptable carrier and a replication defective herpesvirus which expresses a heterologous protein to which an immune response is desired, wherein said herpesvirus is characterized by a mutation in at least one gene encoding HSV-1, ICP27; or HSV-1, ICP8; or in a corresponding early gene in a non-HSV-1 herpesvirus, and the mutation renders the herpesvirus incapable of replication.

10. The immunogenic composition of claim 9, wherein the herpesvirus is HSV-1, HSV-2, VZV, EBV, HHV-6 or HHV-7.

11. The immunogenic composition of claim 9 wherein the gene is HSV-1 ICP-27.

12. The immunogenic composition of claim 9 wherein said gene is HSV-1 or HSV-2 ICP-8.

13. The immunogenic composition of claim 9, wherein said herpesvirus is characterized by a mutation in two or more genes encoding HSV-1, ICP27; or HSV-1, ICP8; or in a corresponding early gene in a non-HSV-1 herpesvirus, and the mutation renders the herpesvirus incapable of replication.

14. The immunogenic composition of claim 13, wherein said genes encode ICP8 and ICP 27.

15. The immunogenic composition of claim 9, wherein the gene encoding ICP27 comprises a first mutation and the gene encoding ICP8 comprises a second mutation, thereby, the herpesvirus expressing the heterologous protein is rendered incapable of replication.

16. The immunogenic composition of claim 13, wherein the gene encoding ICP27 comprises a first mutation, thereby, the herpesvirus expressing the heterologous protein is rendered incapable of replication.

17. The immunogenic composition of claim 13, wherein the gene encoding ICP8 comprises a first mutation, thereby, the herpesvirus expressing the heterologous protein is rendered incapable of replication.

18. The immunogenic composition of claim 13, wherein the herpesvirus expressing the heterologous protein is HSV-1 or HSV-2.

19. The immunogenic composition of claim 18, wherein the heterologous protein is an immunogenic protein from a virus, bacteria, fungi or parasite.

20. The immunogenic composition of claim 19, wherein the immunogenic protein elicits a B- and/or T-cell immune response.

21. A method of eliciting an immune response in a mammal, the method comprising administering to the mammal an immunogenic composition comprising a mutated herpesvirus, expressing a heterologous protein and is capable of infecting a mammalian cell and eliciting an immune response, wherein the herpesvirus includes a mutation in a gene encoding HSV-1, ICP27; or HSV-1, ICP8; or in a corresponding early gene in a non-HSV-1 herpesvirus, and the mutated herpesvirus is rendered incapable of replication.

22. The method of claim 21, wherein the herpesvirus expressing the heterologous protein is selected from the group consisting of HSV-1, HSV-2, VZV, EBV, HHV-6 and HHV-7.

23. The method of claim 21, wherein the herpesvirus expressing the heterologous protein is HSV-1 or HSV-2.

24. The method of claim 21, wherein the gene encoding ICP27 comprises a first mutation and the gene encoding ICP8 comprises a second mutation, thereby, the herpesvirus expressing the heterologous protein is rendered incapable of replication.

25. The immunogenic composition of claim 9, wherein the heterologous protein is an immunogenic protein from a virus, bacteria, fungi or parasite.

26. The immunogenic composition of claim 25, further comprising a mutation in at least two of the genes.

27. The immunogenic composition of claim 25, further comprising a mutation in at least two of the genes, wherein one mutation is a deletion mutation and the other mutation is a nonsense mutation.

28. A method of treating a mammal to elicit an immunogenic response, the method comprising administering to the mammal an effective amount of an immunogenic composition comprising a mutated herpesvirus expressing a heterologous protein in a pharmaceutically acceptable carrier, wherein the herpesvirus includes a mutation in a gene encoding HSV-1, ICP27; or HSV-1, ICP8; or in a corresponding early gene in a non-HSV-1 herpesvirus, thereby, the mutated herpesvirus is rendered incapable of replication, and the mutant herpesvirus induces an immunogenic effect upon in vivo administration to the mammal.

29. The method according to claim 28, wherein the herpesvirus contains a mutation in at least two of the genes and expresses a heterologous protein.

30. The method according to claim 28, wherein the herpesvirus contains a mutation in at least two of the genes, wherein one mutation is a deletion mutation and the other mutation is a nonsense mutation.

31. The method according to claim 28, wherein the herpesvirus contains at least two mutations in the genes.

32. The method according to claim 31, wherein one mutation is a deletion mutation and the other mutation is a nonsense mutation.

33. The method of claim 28, wherein the heterologous protein is an immunogenic protein from a virus, bacteria, fungi or parasite.

34. The method according to claim 28, wherein the in vivo immunogenic effect in a mammal comprises a B-cell and/or T cell response.

35. An immunogenic composition comprising a pharmaceutically acceptable carrier and a mutated herpesvirus capable of infecting a mammalian cell and of eliciting an immune response in a mammal immunized with the composition, wherein the herpesvirus includes two or more mutations, at least one of the mutations being in genes encoding a protein essential for viral genome replication to render the herpesvirus incapable of replication, wherein one mutation is a nonsense mutation and another mutation is a deletion mutation.

36. The immunogenic composition of claim 35, wherein the herpesvirus is selected from the group consisting of HSV-1, HSV-2, VZV, EBV, HHV-6 and HHV-7.

37. The immunogenic composition of claim 35, wherein the herpesvirus is HSV-1 or HSV-2.

38. The immunogenic composition of claim 36, wherein a gene encoding ICP27 comprises a nonsense mutation and a gene encoding ICP8 comprises a deletion mutation.

* * * * *